(12) United States Patent
Lee et al.

(10) Patent No.: US 7,148,334 B2
(45) Date of Patent: Dec. 12, 2006

(54) COMPOSITION FOR PROTECTING PROTEINS DEGRADATION COMPRISING SMALL HEAT SHOCK PROTEINS (SHSPS) AND METHOD OF TWO-DIMENSIONAL GEL ELECTROPHORESIS USING THE SHSPS

(75) Inventors: Sang Yup Lee, Daejeon (KR); Mee-Jung Han, Daejeon (KR); Si Jae Park, Daejeon (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 10/791,059

(22) Filed: Mar. 2, 2004

(65) Prior Publication Data

US 2005/0123994 A1    Jun. 9, 2005

(30) Foreign Application Priority Data

Sep. 8, 2003    (KR) .................... 10-2003-0062756

(51) Int. Cl.
*C07K 1/26* (2006.01)
(52) U.S. Cl. ..................... 530/412; 530/350
(58) Field of Classification Search ............... 530/350; 435/69.1; 436/178
See application file for complete search history.

(56) References Cited

U.S. PATENT DOCUMENTS

| | | | |
|---|---|---|---|
| 5,993,627 A | 11/1999 | Anderson et al. | |
| 6,123,821 A | 9/2000 | Anderson et al. | |
| 6,136,173 A | 10/2000 | Anderson et al. | |
| 6,245,206 B1 | 6/2002 | Anderson et al. | |
| 6,398,932 B1 | 6/2002 | Anderson et al. | |
| 6,416,644 B1 | 7/2002 | Anderson et al. | |
| 6,554,991 B1 | 4/2003 | Goodman et al. | |
| 2001/0015320 A1 | 8/2001 | Anderson et al. | |
| 2001/0023826 A1 | 9/2001 | Anderson et al. | |
| 2001/0032786 A1 | 10/2001 | Anderson et al. | |
| 2002/0098595 A1* | 7/2002 | Lubman et al. ............. | 436/178 |
| 2002/0133300 A1 | 9/2002 | Anderson et al. | |
| 2002/0157954 A1 | 10/2002 | Anderson et al. | |

FOREIGN PATENT DOCUMENTS

| | | |
|---|---|---|
| WO | WO-98/59092 A1 | 12/1998 |
| WO | WO-01/79250 A1 | 10/2001 |
| WO | WO-02/25259 A2 | 3/2002 |
| WO | WO-02-090966 A1 | 11/2002 |

OTHER PUBLICATIONS

Willsie et al., Small Heat Shock Protein p26 Associates With Nuclear Lamins and HSP70 in Nuclei and Nuclear Matrix Fractions From Stressed Cells, J. of Cellular Biochem., (2002), 84, p. 601-614.*
Kitagawa et al., *E.coli* Small Heat Shock Proteins, IbpA and Ibp, Protect Enzymes from Inactivation by Heat and Oxidants, Eur. J. Biochem., (2002), 269, p. 2907-2917.*
Kitagawa, et al., "*Escherichia coli* small heat shock proteins . . . ", Eur. J. Biochem., 269, 2907-1917, 2002.
Lee, et al., "A small heat shock protein stably binds . . . ", EMBO J., 16:659-671, 1997.
Studer, et al., "Chaperone Activity and Homo-Hetero-oligomer . . . ", J. Biol. Chem., 275:37212-37218, 2000.
Horowitz, "a-Crystallin can function as a molecular chaperone", Proc. Natl. Acad. Sci., USA, 89:10449-53, 1992.
Ehrnsperger, et al., "Stabilization of Proteins and Peptides . . . ", Anal. Biochem., 259: 218-225, 1998.
Hochstrasser, et al., "Methods for Increasing the Resolution . . . ", Anal. Biochem., 173:424-435, 1988.
Han, et al., "Proteome Analysis of Metabolically . . . ", J. Bacteriol., 183:301-308, 2001.
Bradford, "A Rapid and Sensitive Method for the Quantitation . . . ", Anal. Biochem. 72:248-254, 1976.
Sambrook, et al., "Molecular Cloning", $2^{nd}$ ed., Cold Spring Harbor Laboratory Press, NY, 1989.

* cited by examiner

*Primary Examiner*—Robert A. Wax
(74) *Attorney, Agent, or Firm*—Steven J. Hultguist; Intellectual Property/Technology Law

(57) ABSTRACT

The present invention relates to a composition containing sHSPs for prevention of protein degradation and a composition for two-dimensional (2-D) gel electrophoresis. Furthermore, the present invention relates to the improved method of 2-D gel electrophoresis, which is characterized by using sHSPs. According to the present invention, decreasing of protein spots was prevented in the 2-D gel electrophoresis, thereby obtaining 2-D gel with much more protein spots.

12 Claims, 15 Drawing Sheets

FIG. 8
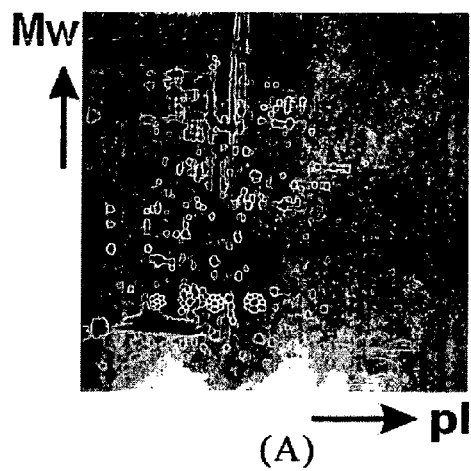
(A)
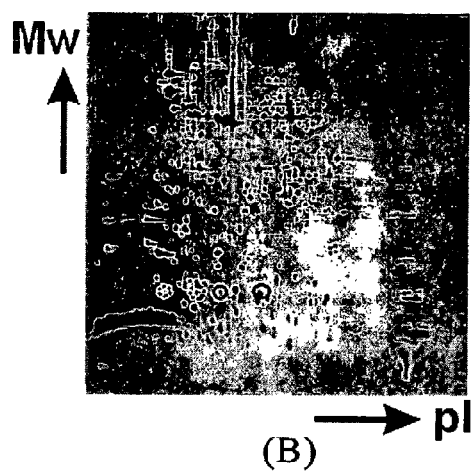
(B)
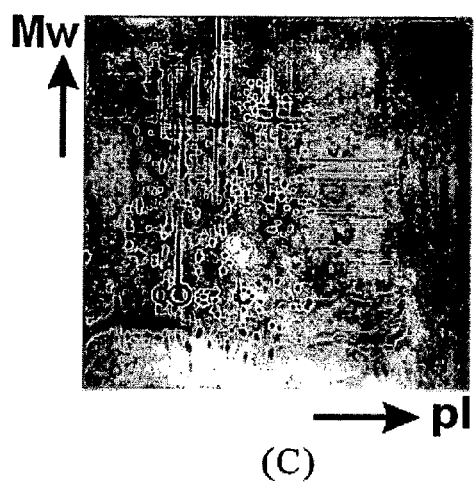
(C)
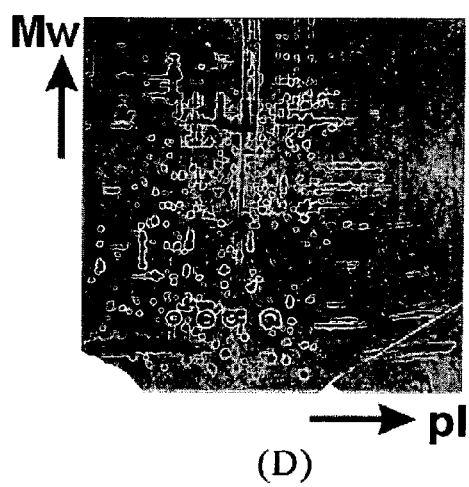
(D)

FIG. 9
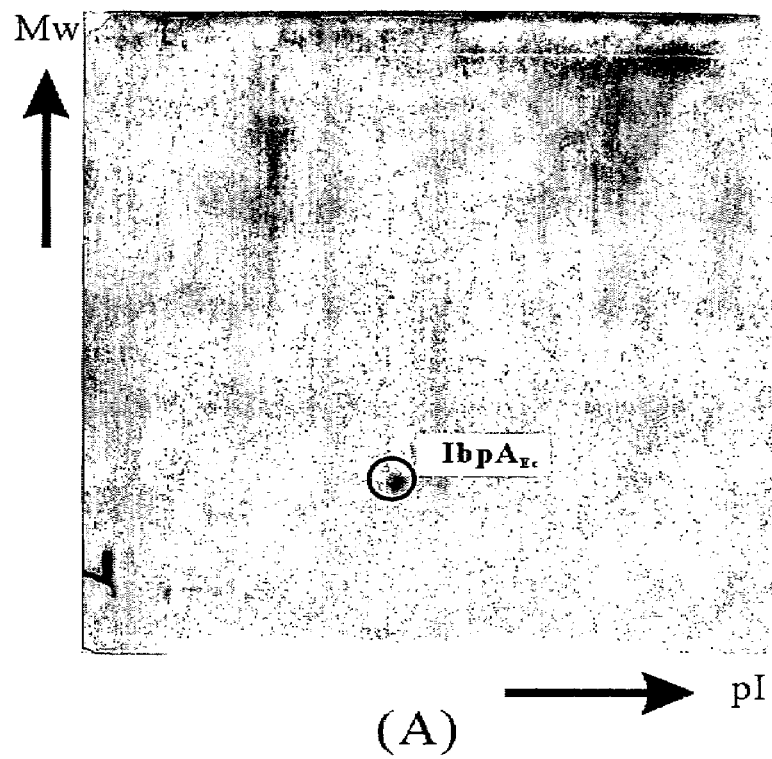
(A)
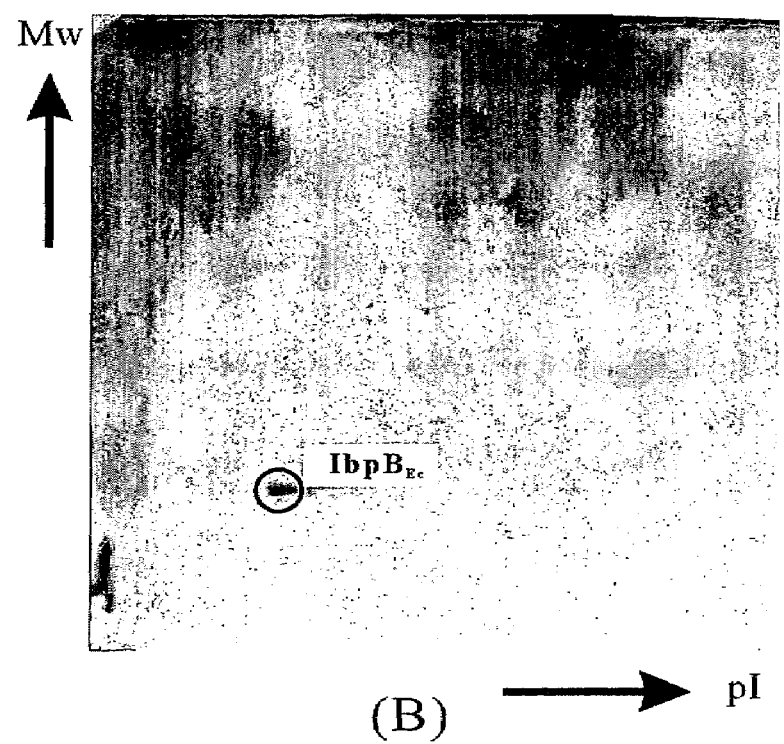
(B)

FIG. 10
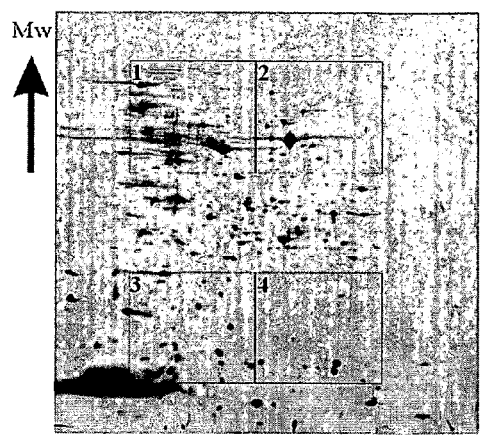
(A)
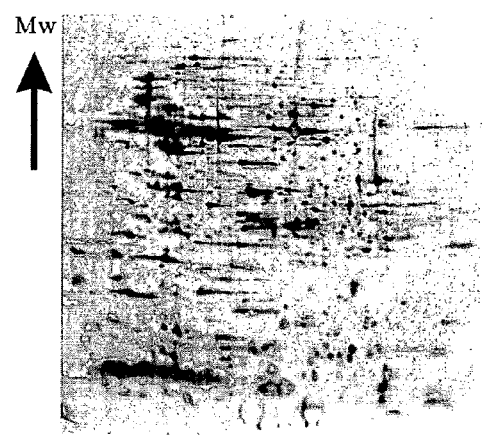
(B)
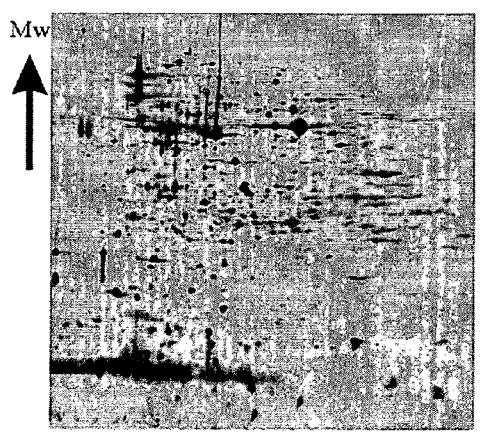
(C)
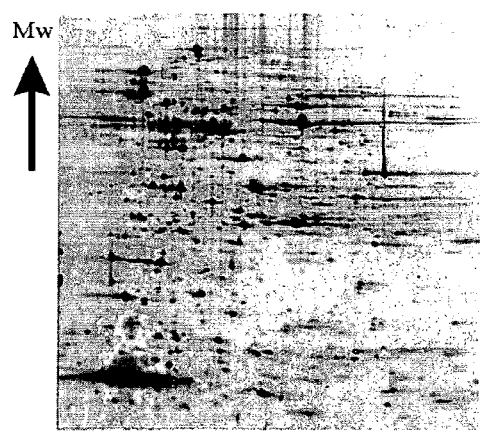
(D)

FIG. 10
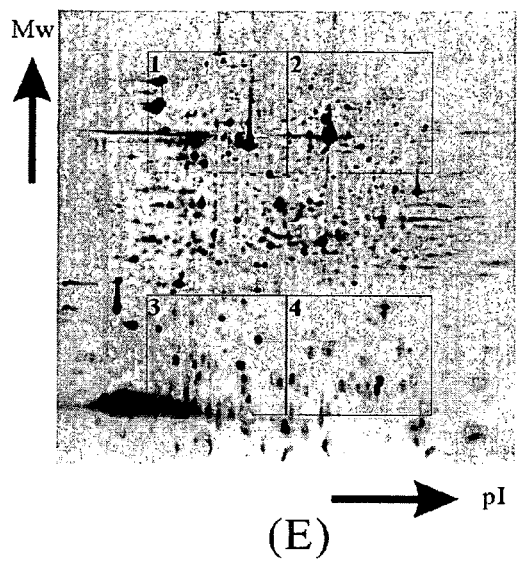
(E)
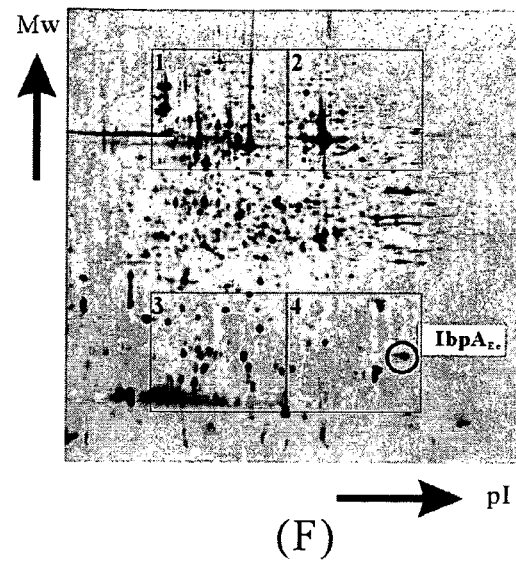
(F)
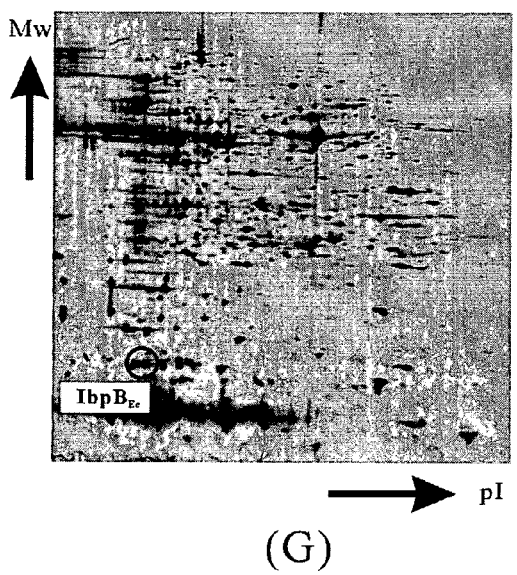
(G)
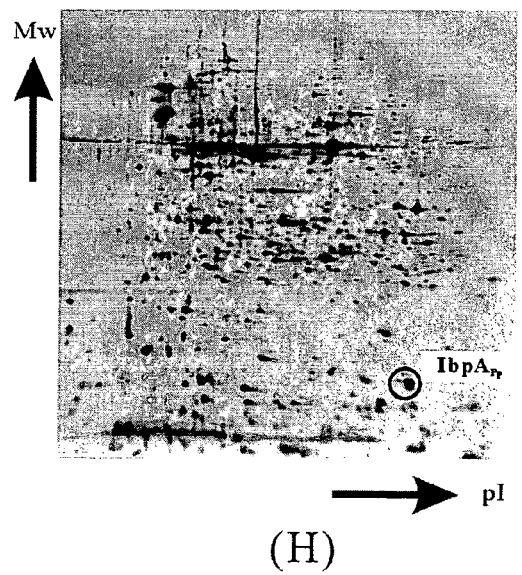
(H)

(I)

FIG. 12
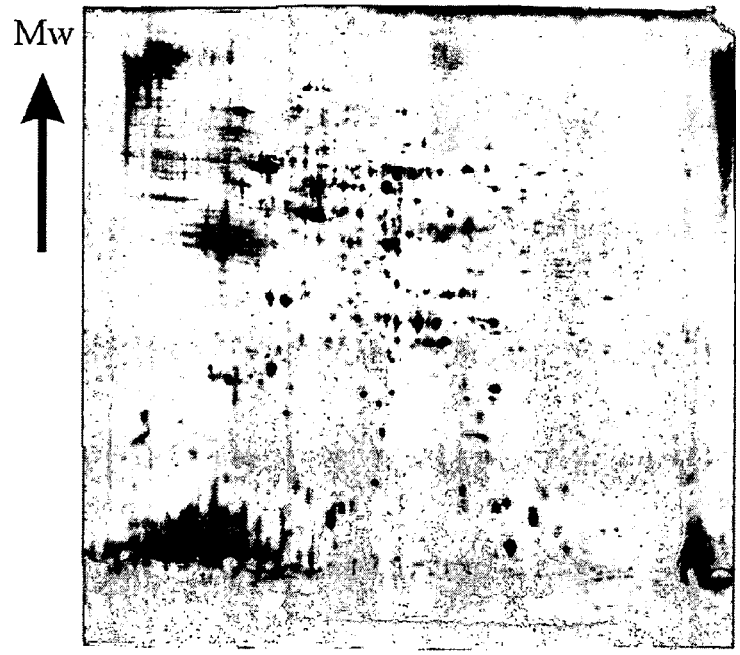
(A)
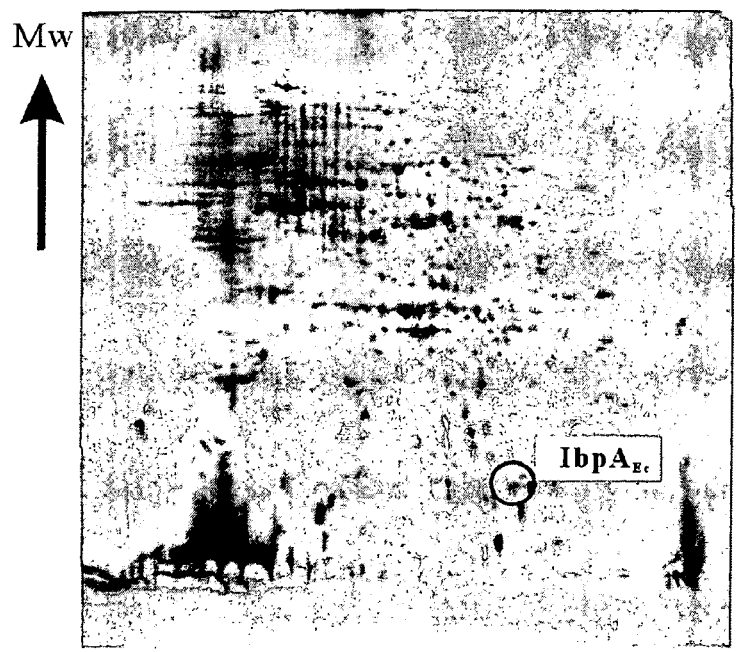
(B)

FIG. 13
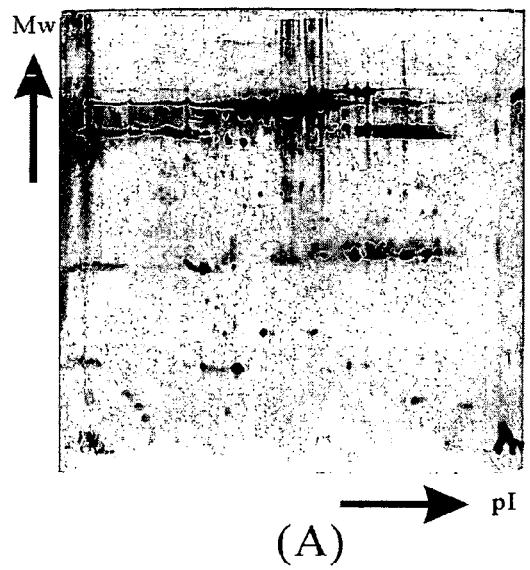
(A)
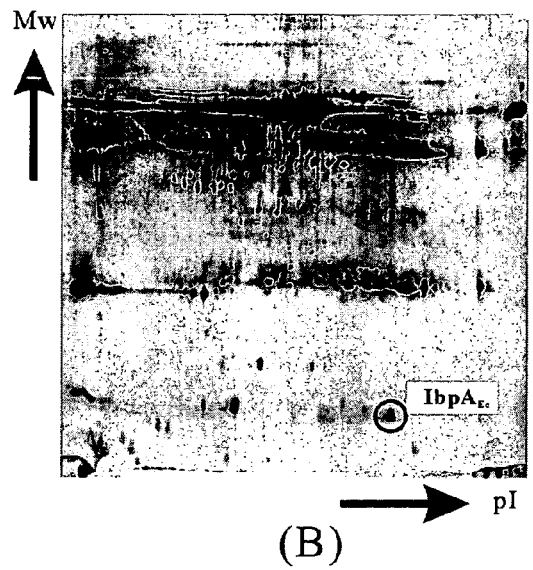
(B)
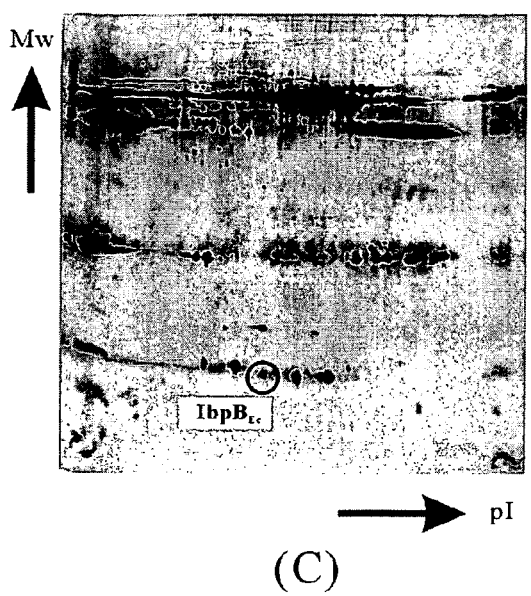
(C)

```
                        SEQUENCE LISTING

<160> NUMBER OF SEQ ID NOS: 8

<210> SEQ ID NO 1
<211> LENGTH: 31
<212> TYPE: DNA
<213> ORGANISM: Artificial Sequence
<220> FEATURE:
<223> OTHER INFORMATION: Synthetic Construct

<400> SEQUENCE: 1
ggaattcatg cgtaactttg atttatcccc g                               31

<210> SEQ ID NO 2
<211> LENGTH: 51
<212> TYPE: DNA
<213> ORGANISM: Artificial Sequence
<220> FEATURE:
<223> OTHER INFORMATION: Synthetic Construct

<400> SEQUENCE: 2
cccaagcttt taatggtgat gatggtgatg gttgatttcg atacggcgcg g          51

<210> SEQ ID NO 3
<211> LENGTH: 34
<212> TYPE: DNA
<213> ORGANISM: Artificial Sequence
<220> FEATURE:
<223> OTHER INFORMATION: Synthetic Construct

<400> SEQUENCE: 3
ggaattcatg cgtaacttcg atttatcccc actg                            34

<210> SEQ ID NO 4
<211> LENGTH: 53
<212> TYPE: DNA
<213> ORGANISM: Artificial Sequence
<220> FEATURE:
<223> OTHER INFORMATION: Synthetic Construct

<400> SEQUENCE: 4
ccaagctttt aatggtgatg atggtgatgg ctatttaacg cgggacgttc gct        53

<210> SEQ ID NO 5
<211> LENGTH: 28
<212> TYPE: DNA
<213> ORGANISM: Artificial Sequence
<220> FEATURE:
<223> OTHER INFORMATION: Synthetic Construct
```

-continued

```
<400> SEQUENCE: 5
ggaattcatg accatgacta ctgctttc                                               28

<210> SEQ ID NO 6
<211> LENGTH: 47
<212> TYPE: DNA
<213> ORGANISM: Artificial Sequence
<220> FEATURE:
<223> OTHER INFORMATION: Synthetic Construct

<400> SEQUENCE: 6
cccaagcttt taatggtgat gatggtgatg gttcagcgct ggttttt                          47

<210> SEQ ID NO 7
<211> LENGTH: 29
<212> TYPE: DNA
<213> ORGANISM: Artificial Sequence
<220> FEATURE:
<223> OTHER INFORMATION: Synthetic Construct

<400> SEQUENCE: 7
ggaattcatg tcatttaaca gtccatttt                                              29

<210> SEQ ID NO 8
<211> LENGTH: 51
<212> TYPE: DNA
<213> ORGANISM: Artificial Sequence
<220> FEATURE:
<223> OTHER INFORMATION: Synthetic Construct

<400> SEQUENCE: 8
cccaagcttt taatggtgat gatggtgatg gttacccac gattcttgag a                      51
```

COMPOSITION FOR PROTECTING PROTEINS DEGRADATION COMPRISING SMALL HEAT SHOCK PROTEINS (SHSPS) AND METHOD OF TWO-DIMENSIONAL GEL ELECTROPHORESIS USING THE SHSPS

CROSS-REFERENCE TO RELATED APPLICATION

This application claims priority under 35 USC § 119 of Korean Patent Application No. 10-2003-0062756 filed Sep. 8, 2003.

BACKGROUND OF THE INVENTION

1. Field of the Invention

The present invention relates to a composition for preventing protein degradation, which contains small heat shock proteins (sHSPs), as well as a composition for use in two-dimensional (2-D) gel electrophoresis. Moreover, the present invention relates to an improved method of 2-D gel electrophoresis, which is characterized by using the sHSPs.

2. Background of the Related Art

As the base sequence of a human genome is revealed and genome information for numbers of microorganisms, lower animals and plants increases daily, proteomics becomes the focus of the next-generation research.

The proteomics that is a science field for studying proteomes systemically is distinguished from genomics. The proteomes signify complete information for the kind and amount of proteins, which are expressed from genomes under specific condition. Thus, the proteomics simultaneously analyzes and identifies various proteins in cells or tissues that are involved in biological phenomenon. Since this proteomic analysis provides results that cannot be found in genome projects or DNA researches, there are studies being conducted to develop diagnostic reagents or therapeutic agents for adult diseases, such as cancer, diabetes, dementia, and heart and circulation system diseases, and mental diseases, using this analysis, and also studies to apply it in fields, such as organ transplantation.

Core technology that has most widely been used in proteomics studies is a 2-D gel electrophoresis technique. The 2-D gel electrophoresis technique is the best method capable of separating and quantifying total proteins in cells or tissues.

The 2-D gel electrophoresis technique is a method where a mixture of proteins is first separated according to the isoelectric point (pI) of each protein, and each of the separated samples is further separated according to its molecular weight in a vertical direction such that the separated proteins are 2-Dly distributed on a plane. Namely, an isoelectric-focusing (IEF) method and a sodium dodecyl sulphate-polyacrylamide gel electrophoresis (SDS-PAGE) method are used respectively.

Currently, 2-D gels using IEF were developed, and commercialized systems appeared one after another, to greatly improve reproducibility that is a problem of the prior 2-D gel (U.S. Pat. No. 6,554,991; U.S. 2002/157954; U.S. 2002/133300; U.S. Pat. Nos. 6,416,644; 6,398,932; WO 02/25259; U.S. 2001/032786; U.S. 2001/023826; U.S. 2001/015320; U.S. Pat. Nos. 6,245,206; 6,136,173; 6,123,821; 5,993,627; WO 98/59092; and WO 02/90966). Furthermore, the steps of staining individual proteins in the 2-D gel and digesting the stained proteins with protease were preformed using an automated system and a computer so that samples could be processed in an easy and simple way.

However, the automation of the 2-D gel electrophoresis which is the first step is not yet realized. Moreover, since there is protein loss in all the process of the 2-D gel electrophoresis, it is impossible to completely analyze complex proteomes in cells or tissues. If cells are lysated in a first step, as protease is released from the cells protein degradation occurs to reduce the total number of proteins.

For this reason, a variety of the following methods for inhibiting protease attack in a protein separation process were designed: (1) the direction addition of strong denaturants to samples; (2) the preparation of samples at a low temperature or an alkaline condition (above pH 9); and (3) the use of protease inhibitor. Examples of the protease inhibitor include phenylmethyl-sulphonyl fluoride (PMSF), aminoethyl benzylsufonyl fluoride or Pefabloc™ SC (AEBSF), ethylenediaminetetraacetic acid (EDTA), benzamidine, tosyl lysine chloromethyl ketone (TLCK), and tosyl phenylalanine chloromethyl ketone (TPCK). However, in such methods, proteolysis cannot be completely inhibited, and the kinds and origins of samples are very various such that an optimal process for preparing the samples should be empirically determined.

Meanwhile, sHSPs that are heat shock proteins (HSPs) with a low molecular weight of 15–30 kDa are induced by stress such as heat shock or the overproduction of certain proteins, and act to prevent protein denaturation. One or more of the sHSPs are present in each of all organisms from eukaryotes to prokaryotes, and the sHSPs known till now are given in Table 1 below.

TABLE 1

| The sHSPs known. | |
|---|---|
| Origin | sHSPs |
| *Agrobacterium tumefaciens* str. C58 (U. Washington) | IbpA |
| *Arabidopsis thaliana* | SHSPs |
| *Bradyrhizobium japonicum* | HspB, HspH, HspC, HspF |
| *Brucella suis* 1330 | IbpA |
| *Buchnera aphidicola* plasmid pBPS1 | sHSPs |
| *Buchnera aphidicola* str. APS (*Acyrthosiphon pisum*) | IbpA |
| *Citrus tristeza* virus | sHSPs |
| *Escherichia coli* CFT073 | IbpA, IbpB |
| *Escherichia coli* K12 | IbpA, IbpB |
| *Escherichia coli* O157: H7 EDL933 | IbpA, IbpB |
| *Escherichia coli* O157: H7 | IbpA, IbpB |
| *Helicobacter pylori* 26695 | IbpB |
| Human | Hsp27, α, β-crystallin |
| *Methanococcus jannaschii* | HSP16.5 |
| *Methanopyrus kandleri* AV19 | IbpA |
| Murine | Hsp25 |
| *Mycobacterium leprae* strain TN | sHSPs |
| *Mycobacterium tuberculosis* | Hsp16.3 |
| *Pirellula* sp. | IbpB |
| *Pisum sativum*(pea) | Hsp18.1 |
| *Plasmodium falciparum* 3D7 | sHSPs |
| *Pseudomonas aeruginosa* PA01 | IbpA |
| *Pseudomonas putida* KT2440 | IbpA |
| *Saccharomyces cerevisiae* | Hsp26 |
| *Salmonella enterica* subsp. enterica serovar Typhi | IbpA, IbpB |
| *Salmonella typhimurium* LT2 | IbpA, IbpB |
| *Shewanella oneidensis* MR-1 | IbpA |
| *Shigella flexneri* 2a str. 2457T | IbpA, IbpB |
| *Shigella flexneri* 2a str. 301 | IbpA, IbpB |
| *Sinorhizobium meliloti* 1021 | IbpA |
| *Sinorhizobium meliloti* plasmid pSymA | IbpA |
| *Streptococcus pyogenes* | IbpA |
| *Streptomyces coelicolor* A3(2) | sHSPs |

TABLE 1-continued

The sHSPs known.

| Origin | sHSPs |
| --- | --- |
| Sulfolobus solfataricus | sHSPs |
| Synechococcus vulcanus | Hsp16 |
| Thermoanaerobacter tengcongensis strain MB4T | IbpA |
| Thermoplasma acidophilum | IbpA |
| Yersinia pestis KIM | sHSPs, IbpA, IbpB |
| Yersinia pestis strain CO92 | IbpA, IbpB |

Such sHSPs have a conserved region in an evolutionary process and thus has been performing substantially similar functions. ATP independent sHSPs perform a function of preventing protein aggregation irreversibly by combining with denatured proteins under heat stress condition. Therefore, ATP independent sHSPs return the denatured proteins to the original form by correct refolding in cooperation with ATP dependent HSPs(heat shock proteins). For example, it has been reported that IbpA derived from *E. coli* and IbpB derived from *E. coli* prevent a citrate synthase from being inactivated by blocking aggregation due to heat or oxidant (Kitagawa et al., *Eur. J. Biochem.*, 269:2907–17, 2002). It has been reported that HSP18.1 derived from pea has a function of blocking aggregation of proteins, such as malate dehydrogenase(MDH), glyceraldehydes-3-phosphate dehydrogenase, etc. under heat stress condition (Lee et al., *EMBO J.*, 16:659–71, 1997). It has been reported that sHSPs derived from *Bradyrbizobium japonicum* has a function of blocking aggregation of citrate synthase due to heat (Studer and Narberhaus, *J. Biol. Chem.*, 275:37212–8, 2000). It has been reported that a α-crystallin derived from human helps correct refolding of target proteins, which is denatured due to heat stress, by preventing aggregation in the process of dialysis (Horwitz, J., *Proc. Natl. Acad. Sci. USA*, 89:10449–53, 1992). Besides, a Pfu-sHSP purified from heat stable organism stabilizes Taq polymerase and enzyme at the high temperature because it protects cell proteins under heat stress condition in the process of PCR (WO 01/79250 A1). Moreover, sHSP 25 derived from Murine stabilizes unstable proteins or peptides in a diagnostic assay (Ehrnsperger et al., *Anal. Biochem.*, 259:218–25, 1998). However, it was not yet known that these sHSPs prevent protein degradation.

Accordingly, the present inventors have conducted intensive studies to develop a method for preventing proteins from being degraded upon 2-D gel electrophoresis, and consequently, first found that the sHSPs had the effect of preventing protein degradation, and also if 2-D gel electrophoresis is performed using such sHSPs, gels with a significantly increased number of protein spots could be obtained, thereby achieving the present invention.

SUMMARY OF THE INVENTION

Therefore, a main object of the present invention is to provide a composition for preventing protein degradation.

Another object of the present invention is to provide a composition for use in 2-D gel electrophoresis, by which protein degradation is prevented and gels having an increased number of spots are obtained.

Still another object of the present invention is to provide a 2-D gel electrophoresis method in which protein degradation is prevented and gels with an increased number of spots are obtained.

To achieve the above objects, in one embodiment, the present invention provides a composition for preventing protein degradation, which contains an effective amount of small heat shock proteins (sHSPs).

In another embodiment, the present invention provides a composition for use in 2-D gel electrophoresis, which contains an effective amount of sHSPs.

In still another embodiment, the present invention provides a method for the 2-D gel electrophoresis for a protein mixture, which comprises the steps of: adding sHSPs to the protein mixture, so as to prevent protein degradation and obtain gels with an increased number of spots; and subjecting the protein mixture containing the sHSPs to 2-D gel electrophoresis.

In still another embodiment, the present invention provides a method for the analysis of proteomes by 2-D gel electrophoresis, which is characterized by using the inventive composition.

In further another embodiment, the present invention provides a method for using sHSPs as inhibitors of target protein degradation by protease.

In the present invention, the sHSPs are preferably one or more selected from the proteins set forth in Table 1 above, and more preferably one or more selected from the group consisting of inclusion body-associated protein A (IbpA), IbpB, IbpAB and HSP26.

In the present invention, the protein mixture, which is used in the 2-D gel electrophoresis method, is preferably total protein in certain cells. The certain cells are preferably prokaryotes or eukaryotes. The prokaryotes are preferably *E. coli* or *Pseudomonas* sp. microorganisms, and the eukaryotes are preferably human-derived cells.

In the present invention, protein degradation represents a chemical reaction in which a mixture of amino acids or peptides is produced by hydrolysis of peptide bond with protease in vivo or in vitro.

In the present invention, the amount of the sHSPs that is added for the prevention of protein degradation is preferably in a range of 0.1 to 50 parts by weight, and more preferably 0.5 to 20 parts by weight, relative to 100 parts by weight of the total protein of an electrophoresis sample. If the sHSPs are added at the amount of less than 0.1 part by weight of the sHSPs are added, it is absolutely insufficient for the prevention of protein degradation, and if they are added at the amount of more than 20 parts by weight of them are added, an excess of the sHSPs either interferes with the separation of the proteins of certain cells to be separated, or cause an adverse effect in view of the purification cost of the sHSPs.

BRIEF DESCRIPTION OF THE DRAWINGS

FIG. 8 represents 2-D gel electrophoretic pictures of transformed *E. coli* WIB101 in which IbpA and/or IbpB is overexpressed in vivo. (A) represents *E. coli* WIB101 (p184ΔCm), (B) represents *E. coli* WIB101(pACTacIbpA), (C) represents *E. coli* WIB101(pACTacIbpB) and (D) represents *E. coli* WIB101(pACTacIbpAB).

FIG. 9 represents 2-D gel electrophoretic pictures of purified IbpA and IbpB protein. (A) and (B) represent IbpA and IbpB, respectively.

FIG. 12 represents 2-D gel electrophoretic pictures of *Pseudomonas putida* KT2440 adding sHSP in vitro. (A) represents *Pseudomonas putida* KT2440 as a control, and (B) represents the case of adding 10 μg of IbpA protein to *Pseudomonas putida* KT2440.

FIG. 13 represents 2-D gel electrophoretic pictures of human serum adding sHSP in vitro. (A) represents human serum as a control, (B) represents the case of adding 10 μg of IbpA protein to human serum and (C) represents the case of adding 10 μg of IbpB protein to human serum.

DETAILED DESCRIPTION OF THE PREFERRED EMBODIMENT

Figure 1:
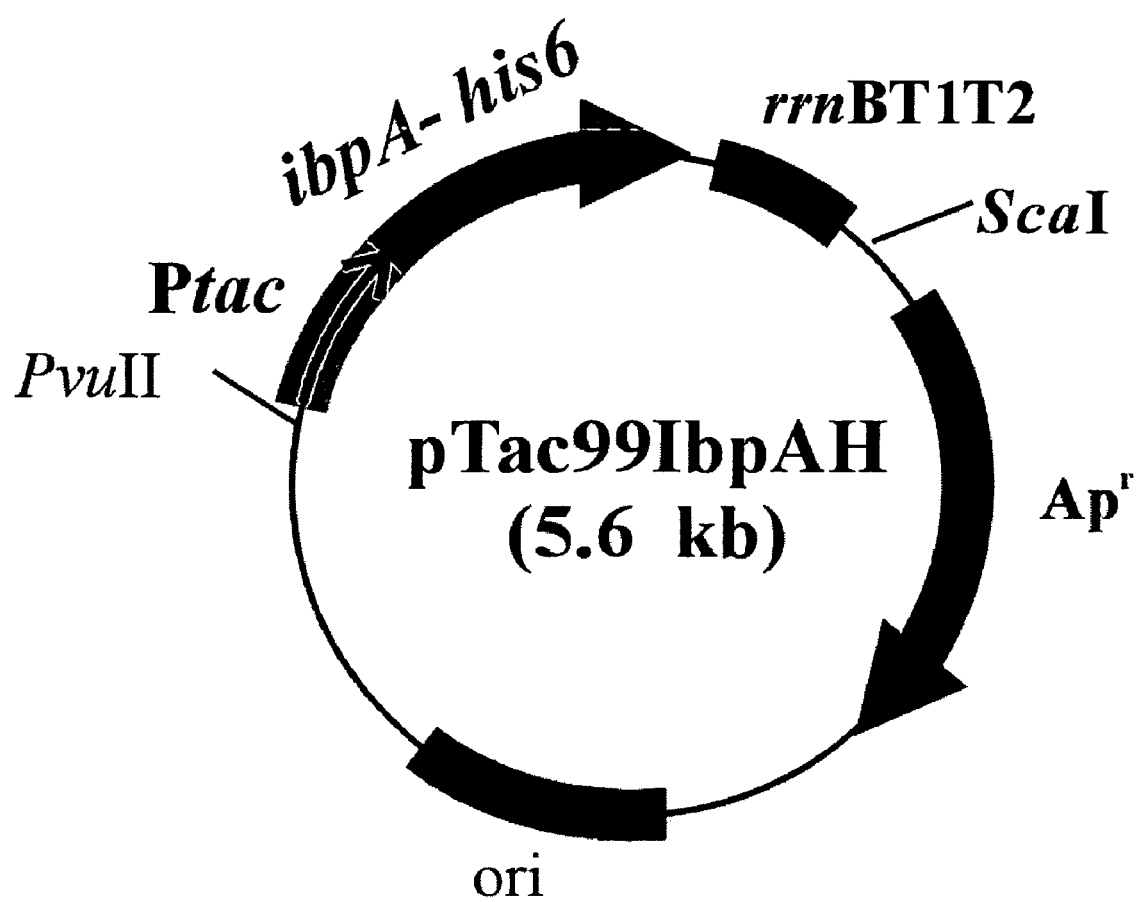
FIG. 1 is a gene map of plasmid pTac99IbpAH.
Figure 2:
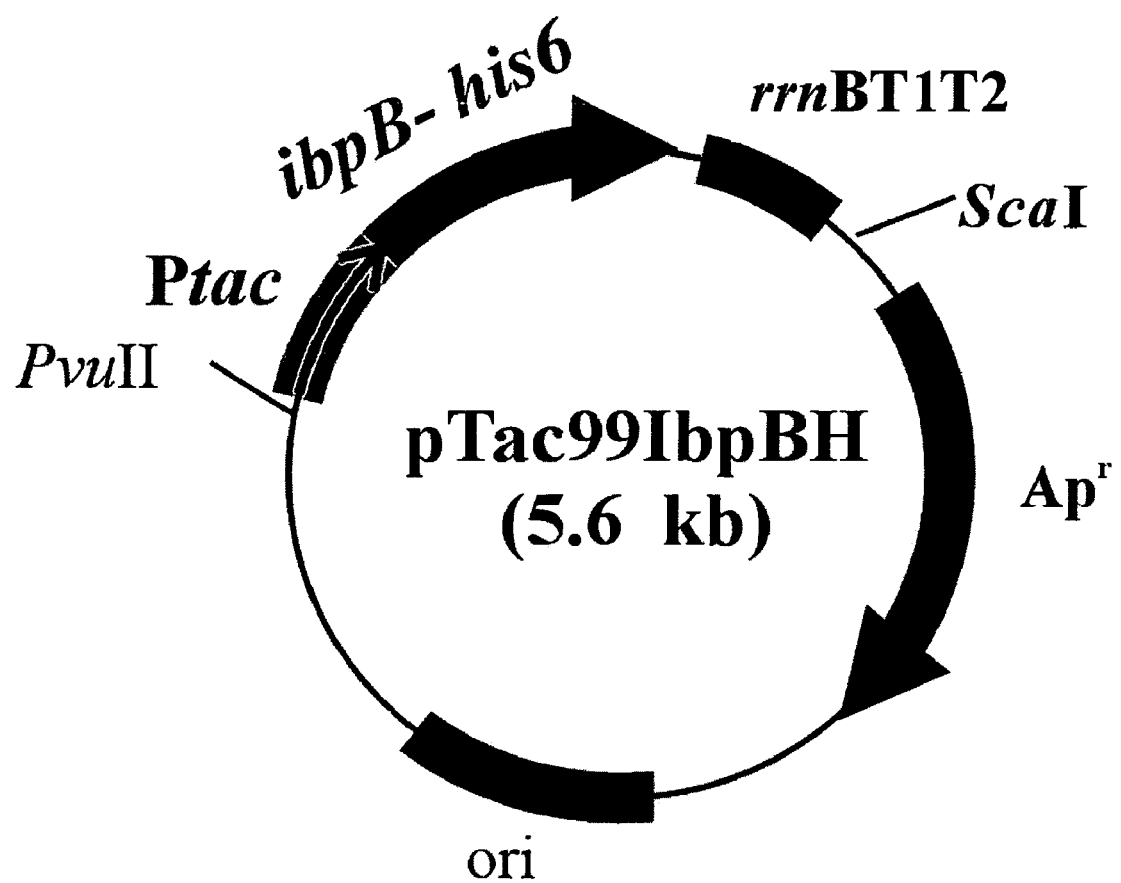
FIG. 2 is a gene map of plasmid pTac99IbpBH.
Figure 3:
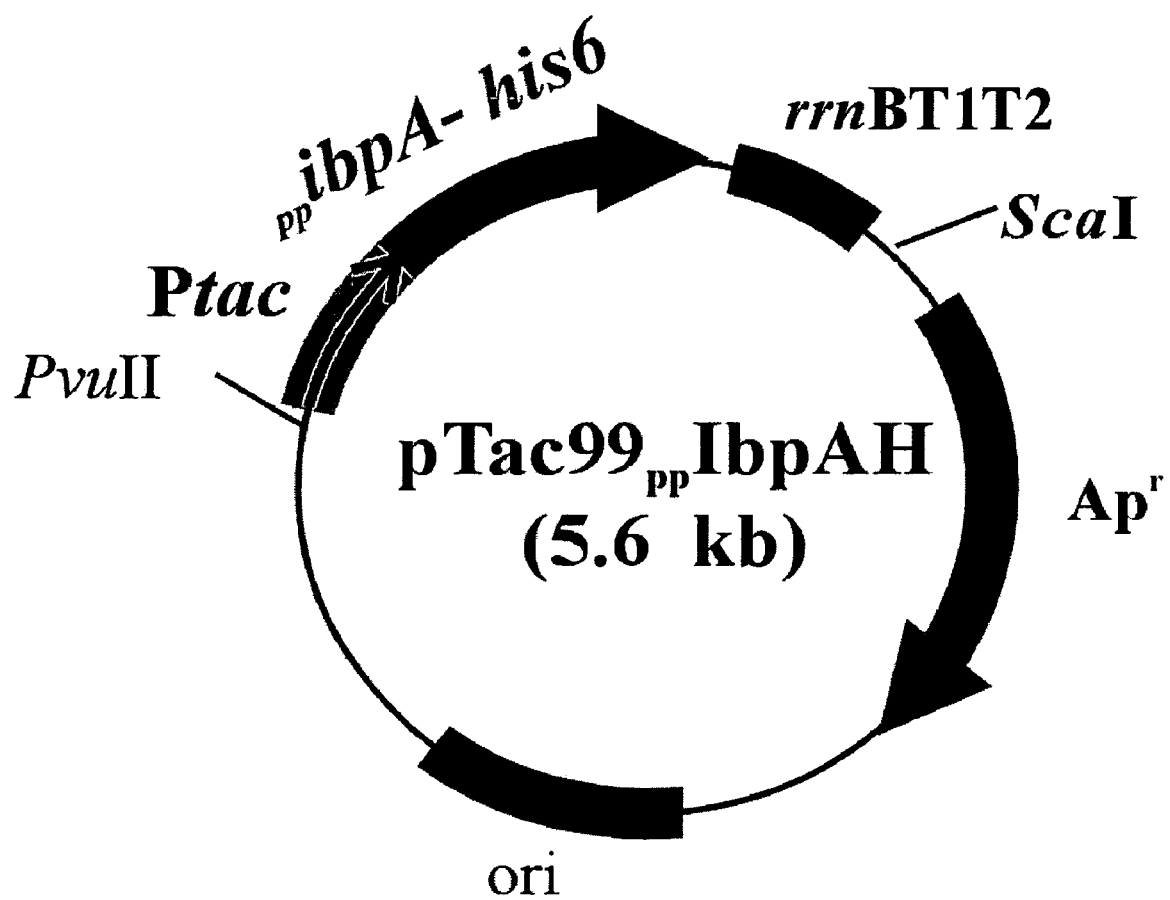
FIG. 3 is a gene map of plasmid pTac99$_{PP}$IbpAH.
Figure 4:
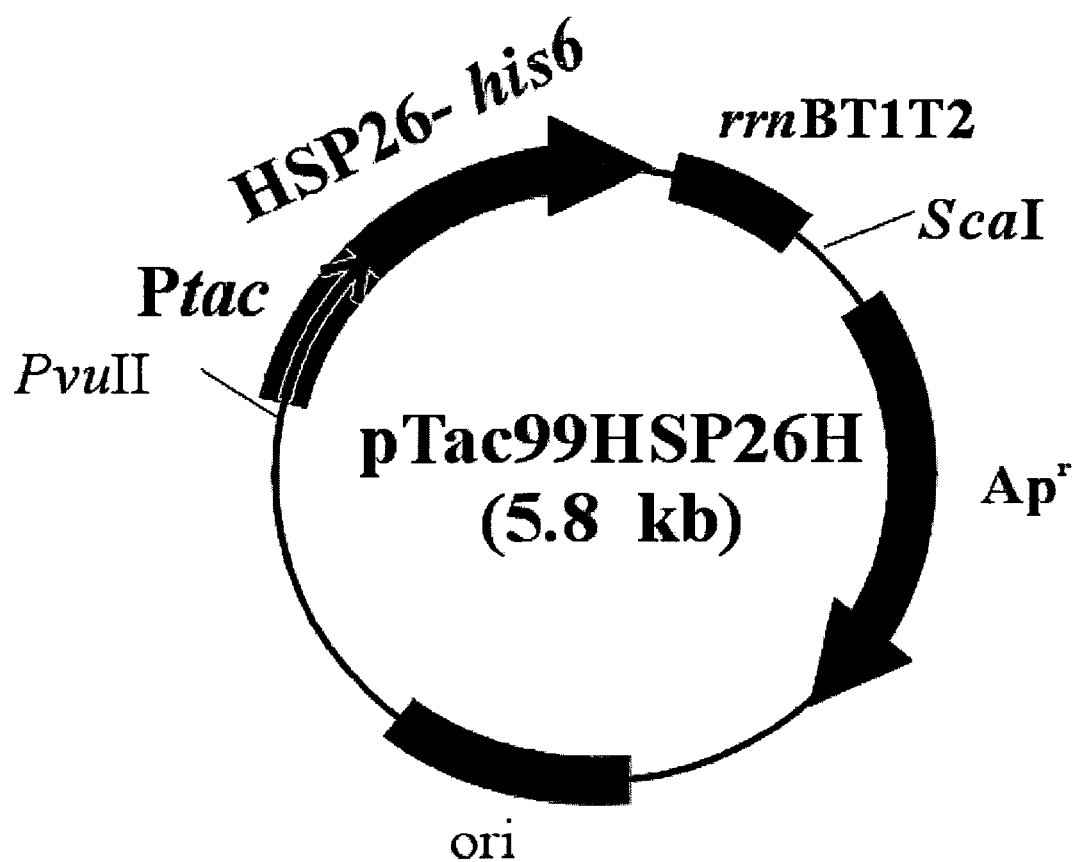
FIG. 4 is a gene map of plasmid pTac99HSP26H.

The present invention will hereinafter be described in further detail by examples. It will however be obvious to a person skilled in the art that the present invention is not limited to the examples.

Particularly, the examples herein are intended to illustrate IbpA or IbpB derived from *E. coli*, IbpA derived from *Pseudomonas* and HSP26 derived from *Saccharomyces cerevisiae* as sHSPs, however it should be borne in mind the sHSPs of Table 1 can be used to the present invention without limitation.

EXAMPLE 1

Preparation of Recombinant Plasmid Containing ibpA, ibpB or HSP26 Gene

Chromosomal DNAs of *E. coli* W3110(ATCC 39936), *Pseudomonas putida* KT2440(ATCC 47054) and *Saccharomyces cerevisiae* were isolated and purified according to a method of Sambrook et al. (Molecular Cloning, 2nd ed., Cold Spring Harbor Laboratory Press, NY, 1989).

*E. coli* W3110, *Pseudomonas putida* KT2440 and *Saccharomyces cerevisiae* were cultured in 500 mL LB(Luria-Bertani) medium for 24 hours, respectively. The strains of early log phase were collected by centrifugation, and then, suspended in 50 ml TE solution (10 mM Tris, 1 mM EDTA; pH 7.6) containing 10 mg/ml lysozyme (Sigma Co., USA). The strain suspensions were cultured at room temperature for 24 hours with slow stirring.

In order to disrupt the strain and remove proteins, the culture broth was added with 16 ml of 10% SDS (sodium dodecyl sulfate) solution and 570 μl of 20 mg/ml Proteinase K (Sigma Co., USA), followed by reaction at 37° C. for one hour. Next, 14 ml of 5M NaCl solution and 10.66 ml of 10% CTAB(cetyltrimethylammoniumbromide, Sigma Co., USA) dissolved in 0.7M NaCl solution, were added and then reacted at 65° C. for 10 minutes. After this, chloroform-isoamylalcohol (24:1) of the same volume as the reaction solution was added to the reaction solution and carefully mixed at room temperature for 2 hours. The mixed solution was centrifuged at 6,000 rpm for 10 minutes, and the supernatant was transferred into a beaker, to which cooled ethanol that is 2-fold larger volume than the supernatant was added slowly to precipitate chromosomal DNA. The precipitated DNA was rolled up around a glass rod. The glass rod was air-dried to remove ethanol, and the chromosomal DNA was dissolved in 1 ml TE solution.

RNase(Sigma Co., USA) was added to the DNA solution to a final concentration of 50 μg/mL, followed by reaction at 37° C. for one hour. After the reaction, chloroform-isoamylalcohol (24:1) of the same volume as the reaction solution was added, and carefully mixed at room temperature for 2 hours.

The mixed solution was centrifuged at 6,000 rpm for 10 minutes, and the supernatant was transferred into a beaker, to which cooled ethanol that is 2-fold larger volume than the supernatant added slowly to precipitate chromosomal DNA. The precipitated DNA was rolled up around a glass rod. The glass rod was air-dried to remove ethanol, and finally, the chromosomal DNAs of purified *E. coli* W3110, *Pseudomonas putida* KT2440 and *Saccharomyces cerevisiae* were dissolved in 1 ml TE solution, respectively.

For easy expression and purification of IbpA, IbpB or HSP26 protein, the recombinant plasmids, pTac99 IbpAH, pTac99IbpBH, pTac99$_{PP}$IbpAH, and pTac99HSP26H, were constructed as follow.

Using the chromosomal DNA of *E. coli* W3110 as a template, PCRs were conducted with primers of SEQ ID NOs: 1 and 2, and primers of SEQ ID NOs: 3 and 4, thereby obtaining ibpA-6his and ibpB-6his genes derived from *E. coli*, respectively.

Furthermore, using the chromosomal DNA of *Pseudomonas putida* KT2440 as a template, PCRs were conducted with primers of SEQ ID NOs: 5 and 6, thereby obtaining $_{PP}$ibpA-6his gene derived from *Pseudomonas*. In *Pseudomonas putida* KT2440 genome, ibpB gene is not known, yet.

Using the chromosomal DNA of *Saccharomyces cerevisiae* as a template, PCRs were conducted with primers of SEQ ID NOs: 7 and 8, thereby obtaining HSP26–6his gene derived from *Saccharomyces cerevisiae*.

All PCRs conducted by the following conditions: initial denaturation at 95° C. for 5 minutes; 30 cycles of denaturation at 95° C. for 50 seconds, annealing at 55° C. for one minute, and extension at 72° C. for one minute and 30 seconds; and final extension at 72° C. for 5 minutes.

Each of the obtained ibpA-6his, ibpB-6his, $_{PP}$ibpA-6his and HSP26-6his genes were inserted into recombinant plasmid pTac99A digested with EcoRI and HindIII, thereby constructing plasmids pTac99IbpAH, pTac99IbpBH, pTac99$_{PP}$IbpAH and pTac99HSP26H, respectively (FIG. 1, FIG. 2, FIG. 3 & FIG. 4).

Recombinant plasmid pTac99A was obtained as follows: The trc promoter of pTrc99A (Pharmacia Biotech., Uppsala, Sweden) was converted into the tac promoter of pKK223-3 (Pharmacia Biotech., Uppsala, Sweden). The tac promoter of pKK223-3 was digested with restriction enzymes PvuII and EcoRI, and then the gene fragment of the tac promoter was inserted into pTrc99A digested with the same restriction enzymes.

```
SEQ ID NO: 1:
5'-ggaattcatgcgtaactttgatttatcccg-3'

SEQ ID NO: 2:
5'-cccaagcttttaatggtgatgatggtgatggttgatttcgatacggc
                                              gcgg-3'

SEQ ID NO: 3:
5'-ggaattcatgcgtaacttcgatttatccccactg-3'

SEQ ID NO: 4:
5'-cccaagcttttaatggtgatgatggtgatggctatttaacgcgggac
                                              gttcgct-3'

SEQ ID NO: 5:
5'-ggaattcatgaccatgactactgctttc-3'

SEQ ID NO: 6:
5'-cccaagcttttaatggtgatgatggtgatggttcagcgctggtttt
                                              t-3'
```

-continued

SEQ ID NO: 7:
5'-ggaattcatgtcatttaacagtccatttt-3'

SEQ ID NO: 8:
5'-cccaagctttttaatggtgatgatggtgatggttacccacgattctt
gaga-3'

EXAMPLE 2

Purification of IbpA, IbpB and HSP26 Protein

The recombinant *E. coli* XL1-Blue(Stratagene, USA) transformed with recombinant plasmid pTac99IbpAH, pTac99IbpBH, pTac99$_{PP}$IbpAH or pTac99HSP26H, containing the gene encoding IbpA, IbpB or HSP26 protein prepared in example 1 was cultured in LB medium (yeast extract 5 g/L, tryptophan 10 g/L, NaCl 10 g/L) containing 50 mg/L ampicillin, respectively.

The expressions of IbpA, IbpB and HSP26 protein were induced by adding 1 mM IPTG(isopropyl-β-thiogalactoside) at an optical density(OD) of 0.7 at 600 nm. 4 hours after induction, 1 ml of each of the culture solutions was taken and centrifuged at 4° C. and 6,000 rpm for 5 minutes, the obtained precipitate was washed one time with 0.5 ml TE solution and centrifuged at 4° C. and 6,000 rpm for 5 minutes to obtain a precipitate. The precipitate was suspended in 0.2 ml equilibrium solution (urea 8M, NaH$_2$PO$_4$ 100 mM, Tris 10 mM, pH 8.0), and subjected to ultrasonic homogenization and fractionation.

The above suspended solution was centrifuged at 4° C. and 10,000 rpm for 10 minutes, and the supernatant was collected and passed through Ni-NTA spin column(Qiagen, USA) pre-equilibrated with the equilibrium solution. And then, the solution was centrifuged at 2,000 rpm for 2 minutes. 600 μl washing solution (urea 8M, NaH$_2$PO$_4$ 100 mM, Tris 10 mM, pH 6.3) was passed through the column two times. 200 μl eluent (urea 8M, NaH$_2$PO$_4$ 100 mM, Tris 10 mM, pH 4.5) was inserted into column to purify IbpA, IbpB and HSP26 proteins.

200 μl of each of the solution containing the purified IbpA, IbpB and HSP26 proteins was taken and mixed with 50 μlSDS-PAGE sample solution (25% glycerol, 2% SDS, 14.4 mM 2-mercaptoethanol, 0.1% bromophenyl blue, 60 mM Tris-HCl). The mixed solution was boiled for 10 minutes and was subjected to SDS-PAGE gel electrophoresis in 12% separating gel. Next, the gel was soaked in a staining solution (methanol 40%, acetic acid 10%, 0.25 g/L Coomassie brilliant blue R) for over 2 hours to be stained and soaked two times in a decolorizing solution (40% methanol, 7% acetic acid) for over 2 hours each time to be decolorized (FIG. 5).

Figure 5:
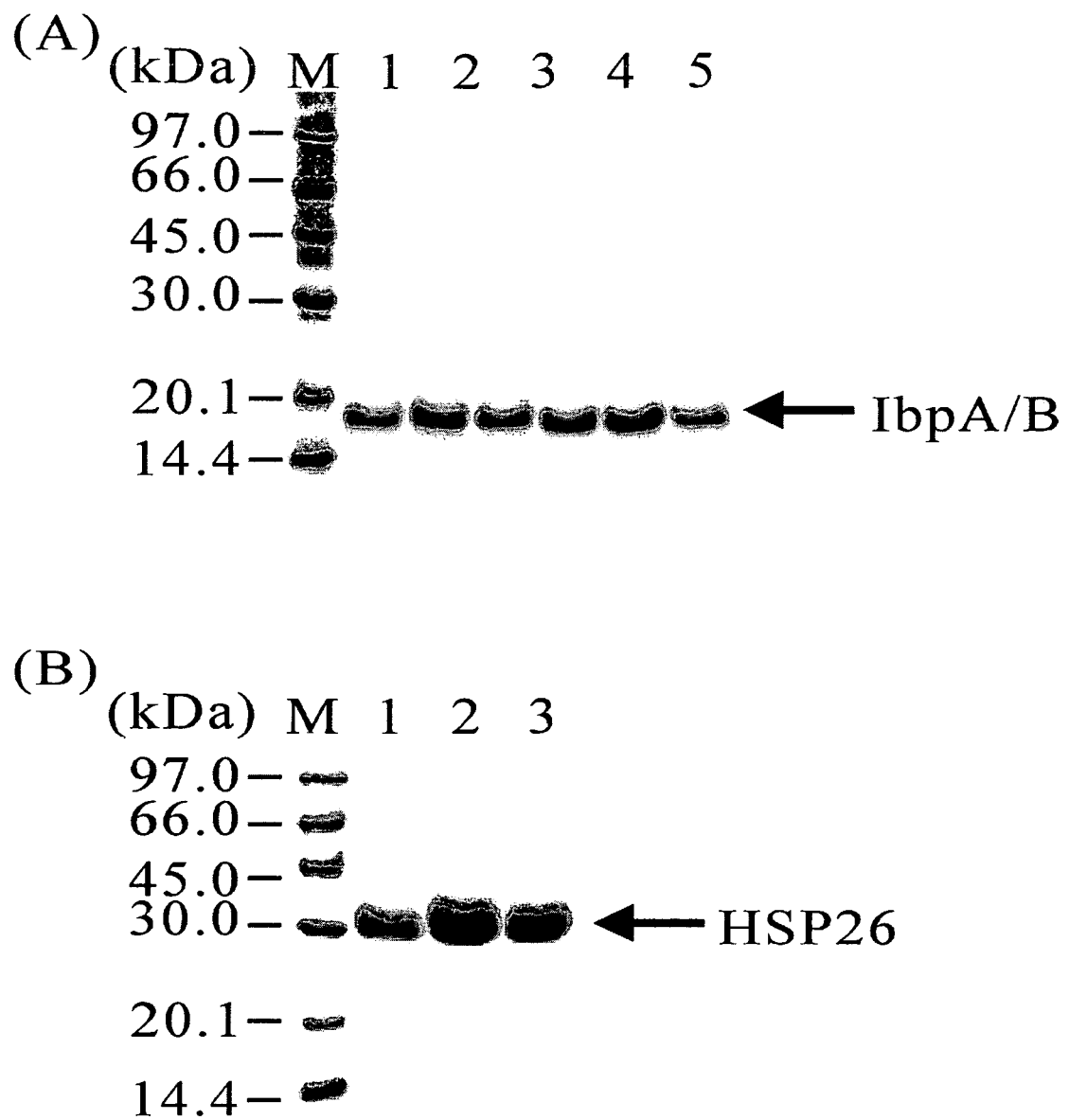
FIG. 5 represents electrophoretic pictures showing the result of protein purification of IbpA, IbpB or HSP26 expressed from recombinant *E. coli* XL1-Blue transformed with recombinant plasmid pTac99IbpAH, pTac99IbpBH, pTac99$_{PP}$IbpAH or pTac99HSP26H. In (A), lane M shows the molecular mass standard, lane 1 and 2 show purified IbpA, lane 3 and 4 show purified IbpB and lane 5 shows purified $_{PP}$IbpA. In (B), lane M shows the molecular mass standard, lane 1 to 3 show purified HSP26.

FIG. 5 represents electrophoretic pictures showing the result of protein purification of IbpA, IbpB and HSP26 expressed from recombinant *E. coli* XL1-Blue transformed with recombinant plasmid pTac99IbpAH, pTac99IbpBH, pTac99$_{PP}$IbpAH or pTac99HSP26H. In FIG. 5(A), lane M shows the standard molecular weight of protein, lane 1 and 2 show purified IbpA, lane 3 and 4 show purified IbpB and lane 5 shows purified $_{PP}$IbpA. In FIG. 5(B), lane M shows standard molecular weight of protein, lane 1 to 3 show purified HSP26. As shown in FIG. 5, the purity of the purified IbpA, IbpB and HSP26 protein was almost 100%.

EXAMPLE 3

The Effect of sHSPs Upon Isolation-purification of Target Protein

Since target proteins are easily attacked by proteases in cell lysis solution, target proteins bring a great loss. In the present invention, the same concentration of human serum albumin as a target protein was diluted in dissolving solution. Then, said protein in solution was incubated with protease, trypsin of various concentrations at room temperature for 2 hours. The enzyme(protease) concentration was changed tor 0, 1/10, 1/20, 1/30 and 1/50 for substrate(target protein). IbpA and IbpB derived from *Escherichia coli*, and HSP26 derived from *Saccharomyces cerevisiae* were used as sHSPs (FIG. 6).

Figure 6:
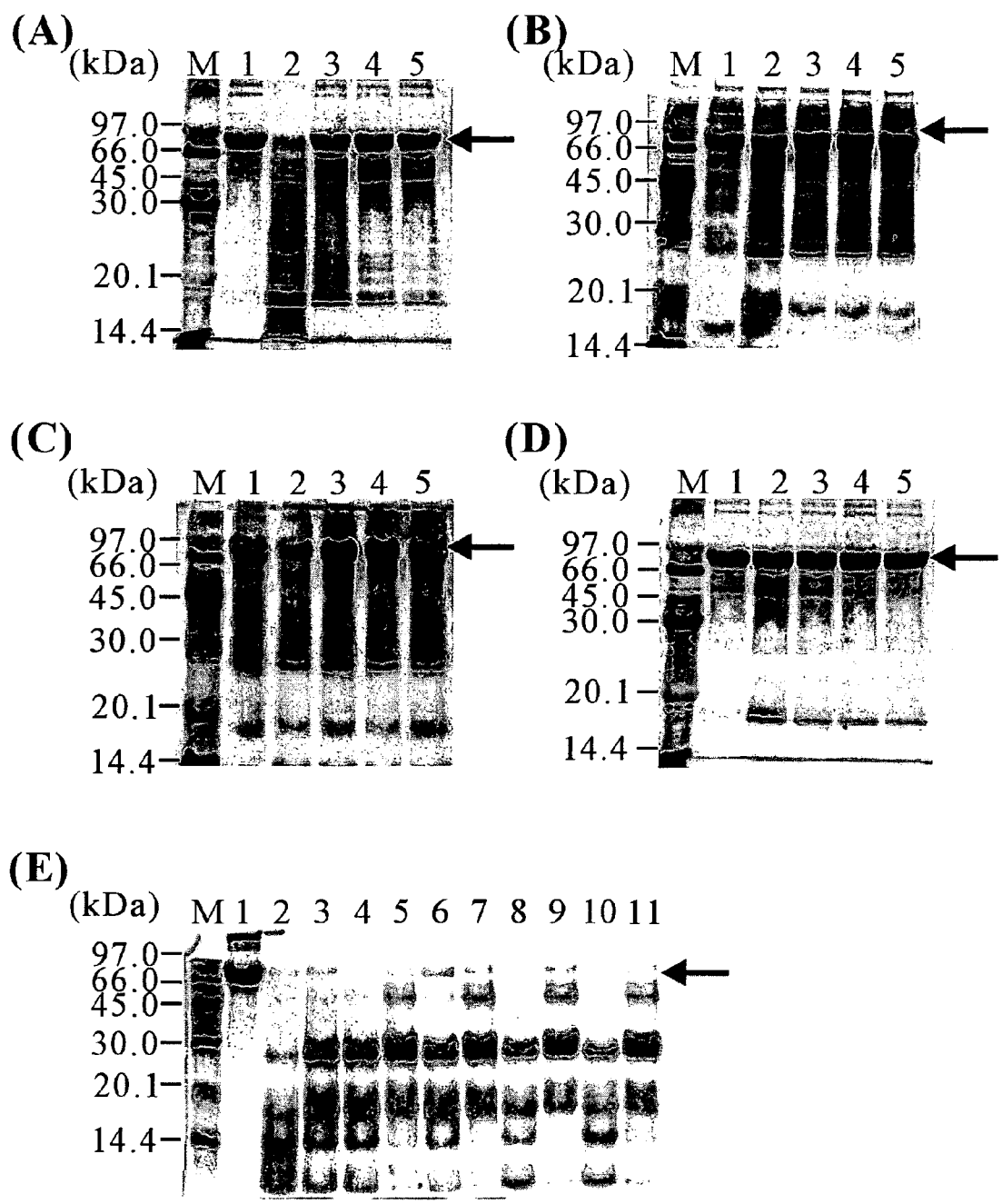
FIG. 6 represents electrophoretic pictures showing the effect of protease inhibition by sHSPs in dissolving solution in which the same volume of human serum albumin is added. (A) represents the dissolving solution as a control in which no sHSPs is added, lane M represents the standard molecular weight of protein, lane 1 represents a dissolving solution in which only 0.5 μg/μl of human serum albumin is added, lane 2 represents a solution in which 0.05 μg/μl of trypsin is added to 0.5 μg/μl of human serum albumin, lane 3 represents a solution in which 0.125 μg/μl of trypsin is added to 0.5 μg/μl of human serum albumin, lane 4 represents a solution in which 0.017 μg/μl of trypsin is added to 0.5 μg/μl of human serum albumin, and lane 5 represents a solution in which 0.01 μg/μl of trypsin is added to 0.5 μg/μl of human serum albumin. (B) represents a dissolving solution in which IbpA is added. (C) represents a dissolving solution in which IbpB is added. (D) represents a dissolving solution in which HSP26 is added. In (B), (C) and (D), lane M represents the standard molecular weight of protein, lane 1 represents a dissolving solution in which only 0.005 μg/μl of sHSP is added to 0.5 μg/μl of human serum albumin, lane 2 represents a solution in which 0.05 μg/μl of trypsin and 0.005 μg/μl of sHSP are added to 0.5 μg/μl of human serum albumin, lane 3 represents a solution in which 0.125 μg/μl of trypsin and 0.005 μg/μl of sHSP are added to 0.5 μg/μl of human serum albumin, lane 4 represents a solution in which 0.017 μg/μl of trypsin and 0.005 μg/μl of sHSP are added to 0.5 μg/μl of human serum albumin, and lane 5 represents a solution in which 0.01 μg/μl of trypsin and 0.005 μg/μl of sHSP are added to 0.5 μg/μl human serum albumin. (E) represents a dissolving solution in which various protease inhibitors are added, lane M represents the standard molecular weight of protein, lane 1 represents a dissolving solution in which only 0.5 μg/μl human serum albumin is added, lane 2 represents a solution in which 0.05 μg/μl trypsin is added to 0.5 μg/μl of human serum albumin, lane 3 represents a solution in which 0.025 μg/μl trypsin is added to 0.5 μg/μl of human serum albumin, lane 4 represents a solution in which 0.05 μg/μl trypsin and 1 mM PMSF are added to 0.5 μg/μl of human serum albumin, lane 5 represents a solution in which 0.025 μg/μl trypsin and 1 mM PMSF are added to 0.5 μg/μl of human serum albumin, lane 6 represents a solution in which 0.05 μg/μl trypsin and 4 mM Pefabloc SC are added to 0.5 μg/μl of human serum albumin, lane 7 represents a solution in which 0.025 μg/μl trypsin and 4 mM Pefabloc SC are added to 0.5 μg/μl of human serum albumin, lane 8 represents a solution in which 0.05 μg/μl trypsin and cocktail inhibitor (7 ml/tablet) are added to 0.5 μg/μl of human serum albumin, lane 9 represents a solution in which 0.025 μg/μl trypsin and cocktail inhibitor (7 ml/tablet) are added to 0.5 μg/μl of human serum albumin, lane 10 represents a solution in which 0.05 μg/μl trypsin and 1 mM EDTA are added to 0.5 μg/μl of human serum albumin, and lane 11 represents a solution in which 0.025 μg/μl trypsin and 1 mM EDTA are added to 0.5 μg/μl of human serum albumin. Human serum albumin is shown with an arrow.

FIG. 6 represents electrophoretic pictures showing the effect of protease inhibition by sHSPs in dissolving solution in which the same volume of human serum albumin is added. (A) represents the dissolving solution as a control in which no sHSPs is added, lane M represents the standard molecular weight of protein, lane 1 represents a dissolving solution in which only 0.5 μg/μl of human serum albumin is added, lane 2 represents a solution in which 0.05 μg/μl of trypsin is added to 0.5 μg/μl of human serum albumin, lane 3 represents a solution in which 0.125 μg/μl of trypsin is added to 0.5 μg/μl of human serum albumin, lane 4 represents a solution in which 0.017 μg/μl of trypsin is added to 0.5 μg/μl of human serum albumin, and lane 5 represents a solution in which 0.01 μg/μl of trypsin is added to 0.5 μg/μl of human serum albumin. (B) represents a dissolving solution in which IbpA is added. (C) represents a dissolving solution in which IbpB is added. (D) represents a dissolving solution in which HSP26 is added. In (B), (C) and (D), lane M represents the standard molecular weight of protein, lane 1 represents a dissolving solution in which only 0.005 μg/μi of sHSP is added to 0.5 μg/μl of human serum albumin, lane 2 represents a solution in which 0.05 μg/μl of trypsin and 0.005 μg/μl of sHSP are added to 0.5 μg/μl of human serum albumin, lane 3 represents a solution in which 0.125 μg/μl of trypsin and 0.005 μg/μl of sHSP are added to 0.5 μg/μl of human serum albumin, lane 4 represents a solution in which 0.017 μg/μl of trypsin and 0.005 μg/μl of sHSP are added to 0.5 μg/μl of human serum albumin, and lane 5 represents a solution in which 0.01 μg/μl of trypsin and 0.005 μg/μl of sHSP are added to 0.5 μg/μl human serum albumin. (E) represents a dissolving solution in which various protease inhibitors are added, lane M represents the standard molecular weight of protein, lane 1 represents a dissolving solution in which only 0.5 μg/μl human serum albumin is added, lane 2 represents a solution in which 0.05 μg/μl trypsin is added to 0.5 μg/μl of human serum albumin, lane 3 represents a solution in which 0.025 μg/μl trypsin is added to 0.5 μg/μl of human serum albumin, lane 4 represents a solution in which 0.05 μg/μl trypsin and 1 mM PMSF are added to 0.5 μg/μl of human serum albumin, lane 5 represents a solution in which 0.025 μg/μl trypsin and 1 mM PMSF are added to 0.5 μg/μl of human serum albumin, lane 6 represents a solution in which 0.05 μg/μl trypsin and 4 mM Pefabloc SC are added to 0.5 μg/μl of human serum albumin, lane 7 represents a solution in which 0.025 μg/μl trypsin and 4 mM Pefabloc SC are added to 0.5 μg/μl of human serum albumin, lane 8 represents a solution in which 0.05 μg/μl trypsin and cocktail inhibitor (7 ml/tablet) are added to 0.5 μg/μl of human serum albumin, lane 9 represents a solution in which 0.025 μg/μl trypsin and cocktail inhibitor (7 ml/tablet) are added to 0.5 μg/μl of human serum albumin, lane 10 represents a solution in which 0.05 µg/µl trypsin and 1 mM EDTA are added to 0.5 µg/µl of human serum albumin, and lane 11 represents a solution in which 0.025 µg/µl trypsin and 1 mM EDTA are added to 0.5 µg/µl of human serum albumin. Human serum albumin is shown with an arrow. As shown in FIG. 6, degradation of human serum albumin was not detected in a solution added by sHSPs. However, most of human serum albumin was degraded by attack of protease in the control group. It was observed that especially human serum albumin was degraded almost completely in trypsin by comparing the lane 2 of FIG. 6(A), FIG. 6(B), FIG. 6(C), and FIG. 6(D). However, there was almost no degradation in case of adding small amount sHSPs. Furthermore, it is revealed that sHSPs can inhibit attacks of proteases more efficiently than conventional protease inhibitors by comparing the lane 2 and lane 3 of FIG. 6(B)–7(D) with the lane 2~lane 11 of FIG. 6(E).

In the present invention, another protease, Proteinase K was used to perform the experiment mentioned above. The same concentration of human serum albumin was diluted in a dissolving solution. Then, the protein in solution was incubated with Proteinase K in various concentrations for 2 hours at room temperature. The concentrations of enzyme (protease) were changed for 0, 1/300, 1/1000, 1/3000, and 1/10000 to substrate(target protein). IbpA and IbpB derived from *Escherichia coli*, and HSP26 derived from *Saccharomyces cerevisiae* were used as sHSPs (FIG. 7).

Figure 7:
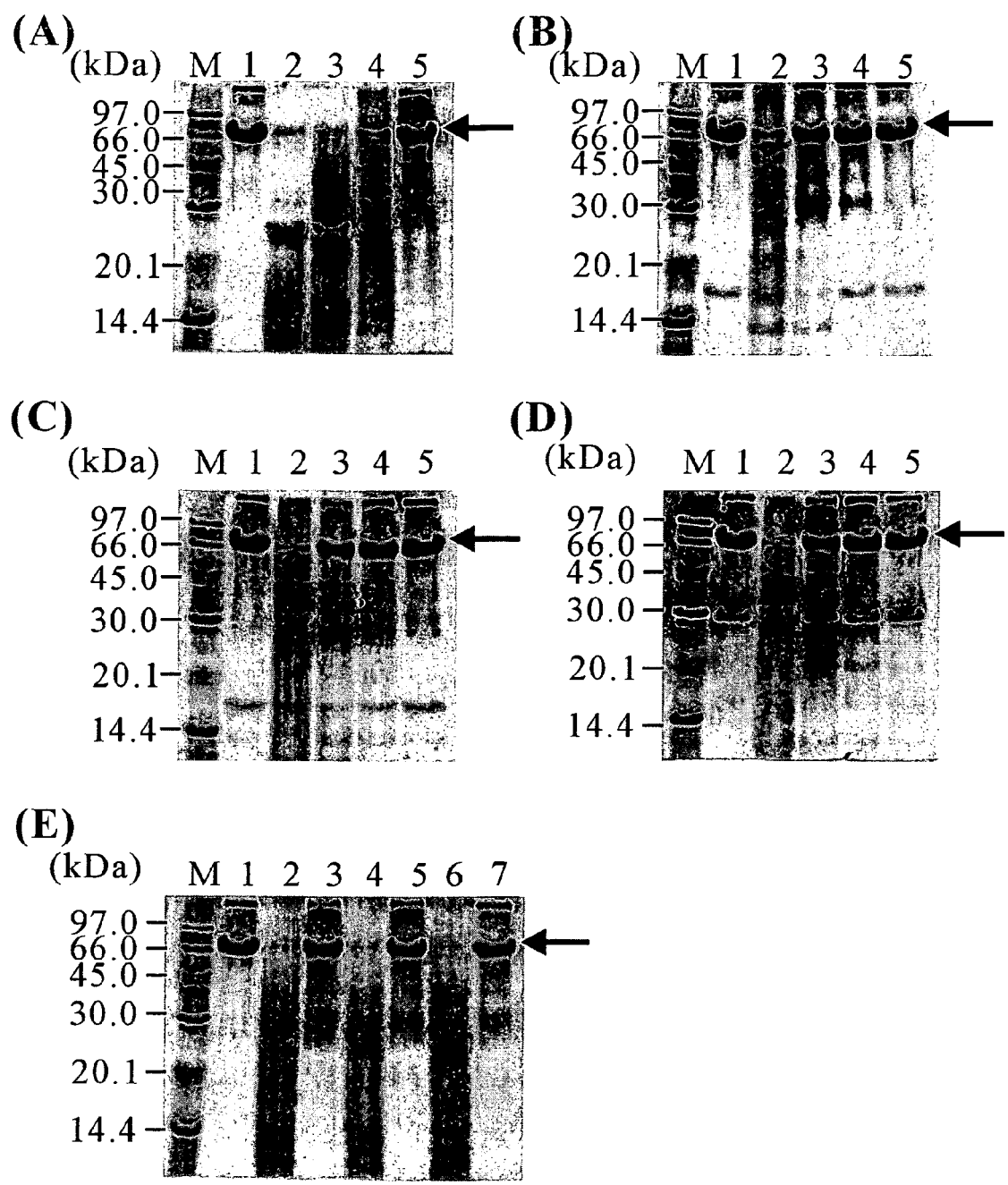
FIG. 7 represents electrophoretic pictures showing the effect of protease inhibition by sHSPs in dissolving solution in which the same volume of human serum albumin is added. (A) represents the dissolving solution as a control in which no sHSPs is added, lane M represents the standard molecular weight of protein, lane 1 represents a dissolving solution in which only 0.5 μg/μl of human serum albumin is added, lane 2 represents a solution in which $1.5 \times 10^{-3}$ μg/μl of Proteinase K is added to 0.5 μg/μl of human serum albumin, lane 3 represents a solution in which $0.5 \times 10^{-3}$ μg/μl of Proteinase K is added to 0.5 μg/μl of human serum albumin, lane 4 represents a solution in which $1.5 \times 10^{-4}$ μg/μl of Proteinase K is added to 0.5 μg/μl of human serum albumin, and lane 5 represents a solution in which $0.5 \times 10^{-4}$ μg/μl of Proteinase K is added to 0.5 μg/μl of human serum albumin. (B) represents a dissolving solution in which IbpA is added. (C) represents a dissolving solution in which IbpB is added. (D) represents a dissolving solution in which HSP26 is added. In (B), (C) and (D), lane M represents the standard molecular weight of protein, lane 1 represents a dissolving solution in which only 0.005 μg/μl of sHSP is added to 0.5 μg/μl of human serum albumin, lane 2 represents a solution in which $1.5 \times 10^{-3}$ μg/μl of Proteinase K and 0.005 μg/μl of sHSP are added to 0.5 μg/μl of human serum albumin, lane 3 represents a solution in which $0.5 \times 10^{-3}$ μg/μl of Proteinase K and 0.005 μg/μl of sHSP are added to 0.5 μg/μl of human serum albumin, lane 4 represents a solution in which $1.5 \times 10^{-4}$ μg/μl of Proteinase K and 0.005 μg/μl of sHSP are added to 0.5 μg/μl of human serum albumin and lane 5 represents a solution in which $0.5 \times 10^{-4}$ μg/μl of Proteinase K and 0.005 μg/μl of sHSP are added to 0.5 μg/μl of human serum albumin. (E) represents a dissolving solution in which various protease inhibitors are added, lane M represents the standard molecular weight of protein, lane 1 represents a dissolving solution in which only 0.5 μg/μl human serum albumin is added, lane 2 represents a solution in which $0.5 \times 10^{-3}$ μg/μl Proteinase K and 4 mM Pefabloc SC are added to 0.5 μg/μl of human serum albumin, lane 3 represents a solution in which $1.5 \times 10^{-4}$ μg/μl Proteinase K and 4 mM Pefabloc SC are added to 0.5 μg/μl of human serum albumin, lane 4 represents a solution in which $0.5 \times 10^{-3}$ μg/μl Proteinase K and cocktail inhibitor (7 ml/tablet) are added to 0.5 μg/μl of human serum albumin, lane 5 represents a solution in which $1.5 \times 10^{-4}$ μg/μl Proteinase K and cocktail inhibitor (7 ml/tablet) are added to 0.5 μg/μl of human serum albumin, lane 6 represents a solution in which $0.5 \times 10^{-3}$ μg/μl Proteinase K and 1 mM EDTA are added to 0.5 μg/μl of human serum albumin and lane 7 represents a solution in which $1.5 \times 10^{-4}$ μg/μl Proteinase K and 1 mM EDTA are added to 0.5 μg/μl of human serum albumin. Human serum albumin is shown with an arrow.

FIG. 7 represents electrophoretic pictures showing the effect of protease inhibition by sHSPs in dissolving solution in which the same volume of human serum albumin is added. (A) represents the dissolving solution as a control in which no sHSPs is added, lane M represents the standard molecular weight of protein, lane 1 represents a dissolving solution in which only 0.5 µg/µl of human serum albumin is added, lane 2 represents a solution in which $1.5 \times 10^{-3}$ µg/µl of Proteinase K is added to 0.5 µg/µl of human serum albumin, lane 3 represents a solution in which $0.5 \times 10^{-3}$ µg/µl of Proteinase K is added to 0.5 µg/µl of human serum albumin, lane 4 represents a solution in which $1.5 \times 10^{4}$ µg/µl of Proteinase K is added to 0.5 µg/µl of human serum albumin, and lane 5 represents a solution in which $0.5 \times 10^{-4}$ µg/µl of Proteinase K is added to 0.5 µg/µl of human serum albumin. (B) represents a dissolving solution in which IbpA is added. (C) represents a dissolving solution in which IbpB is added. (D) represents a dissolving solution in which HSP26 is added. In (B), (C) and (D), lane M represents the standard molecular weight of protein, lane 1 represents a dissolving solution in which only 0.005 µg/µl of sHSP is added to 0.5 µg/µl of human serum albumin, lane 2 represents a solution in which $1.5 \times 10^{-3}$ µg/µl of Proteinase K and 0.005 µg/µl of sHSP are added to 0.5 µg/µl of human serum albumin, lane 3 represents a solution in which $0.5 \times 10^{-3}$ µg/µl of Proteinase K and 0.005 µg/µl of sHSP are added to 0.5 µg/µl of human serum albumin, lane 4 represents a solution in which $1.5 \times 10^{-4}$ µg/µl of Proteinase K and 0.005 µg/µl of sHSP are added to 0.5 µg/µl of human serum albumin and lane 5 represents a solution in which $0.5 \times 10^{-4}$ µg/µl of Proteinase K and 0.005 µg/µl of sHSP are added to 0.5 µg/µl of human serum albumin. (E) represents a dissolving solution in which various protease inhibitors are added, lane M represents the standard molecular weight of protein, lane 1 represents a dissolving solution in which only 0.5 µg/µl human serum albumin is added, lane 2 represents a solution in which $0.5 \times 10^{-3}$ µg/µl Proteinase K and 4 mM Pefabloc SC are added to 0.5 µg/µl of human serum albumin, lane 3 represents a solution in which $1.5 \times 10^{-4}$ µg/µl Proteinase K and 4 mM Pefabloc SC are added to 0.5 µg/µl of human serum albumin, lane 4 represents a solution in which $0.5 \times 10^{-3}$ µg/µl Proteinase K and cocktail inhibitor (7 ml/tablet) are added to 0.5 µg/µl of human serum albumin, lane 5 represents a solution in which $1.5 \times 10^{-4}$ µg/µl Proteinase K and cocktail inhibitor (7 ml/tablet) are added to 0.5 µg/µl of human serum albumin, lane 6 represents a solution in which $0.5 \times 10^{-3}$ µg/µl Proteinase K and 1 mM EDTA are added to 0.5 µg/µl of human serum albumin and lane 7 represents a solution in which $1.5 \times 10^{-4}$ µg/µl Proteinase K and 1 mM EDTA are added to 0.5 µg/µl of human serum albumin. Human serum albumin is shown with an arrow.

As shown in FIG. 7, degradation of human serum albumin was not detected in a solution added by sHSPs. However, most of human serum albumin was degraded by attack of protease in the control group. It was observed that especially human serum albumin was degraded by Proteinase K almost completely by comparing the lane 3 and lane 4 of FIG. 7(A), FIG. 7(B), FIG. 7(C) and FIG. 7(D). However, there was almost no degradation in case of adding small amount sHSPs. Furthermore, it is revealed that sHSPs can inhibit attacks of proteases more efficiently than conventional protease inhibitors by comparing the lane 3 of FIG. 7(B)–7(D) with the lane 2, lane 4 and lane 6 of FIG. 7(E).

EXAMPLE 4

The Effect of IbpA and/or IbpB Upon 2-D Gel Electrophoresis for Proteome Studies The known IbpA and/or IbpB expression plasmid pAC-TacIbpA, pACTacIbpB or pACTacIbpAB and the plasmid p184ΔCm as a control were introduced into the ibpAB gene-deleted mutant *E. coli* WIB101(PCT/KR03/01371), respectively, and then cell-cultured according to the method described in example 2. The expression of IbpA and/or IbpB protein was induced by adding 1 mM IPTG(isopropyl-β-thiogalactoside) at OD of 0.7 at 600 nm. 4 hours after induction, 1 ml of each of the culture broth was taken and centrifuged at 4° C. and 6,000 rpm for 5 minutes, the obtained precipitate was kept at −20° C.

The 2-D gel electrophoresis for each of transformed *E. coli* was performed as follows. 2-D gel electrophoresis is the method of spreading all proteins in a cell using the differences of molecular weight and electric charge, which is the characteristic property of proteins (Hochstrasser et al., *Anal. Biochem.*, 173: 424–35, 1988; Han et al., *J. Bacteriol.*, 183:301–8, 2001).

The 2-D gel electrophoresis were performed using PROTEAN IEF cell and PROTEAN II xi cell(Bio-Rad Laboratories Inc., Herculules, Calif.) in the examples herein.

The sample for 2-D gel electrophoresis was prepared by treating as follows. The culture broth was centrifuged at 4° C. and 6,000 rpm for 5 minutes and the supernatant was spilled out. Then, remaining medium of the precipitate was washed by 500 µl low sodium buffer solution (KCl 3 mM, $KH_2PO_4$ 1.5 mM, NaCl 68 mM, $NaH_2PO_4$ 9 mM). The precipitate was suspended in 100 µl cell lysis buffer (urea 8M, CHAPS 4% (w/v), DTT 65 mM, Tris 40 mM) and centrifuged at 4° C. and 12,000 rpm for 10 minutes, thereby obtaining full proteins.

Proteins were weighed using the Bradford method (Bradford M. M., *Anal. Biochem.*, 72:248–54, 1976). 200 µg protein was dissolved in 340 µl IEF denaturation solution (urea 8M, CHAPS 0.5% (w/v), DTT 10 mM, Bio-lyte pH 3–10 0.2%(w/v), bromophenyl blue 0.001% (w/v)) and inserted into 17 cm ReadyStrip™ IPG Strips pH 3–10(Bio- Rad Laboratories Inc., Herculules, Calif.) to be hydrolyzed for 12 hours at 20° C., then subjected to the isoelectric focusing.

The strip was shaken in equilibrium buffer I (urea 6M, SDS 2% (w/v), Tris-HCl(PH8.8) 0.375M, glycerol 20%(v/v), DTT 130 mM) for about 15 minutes and shaken again in equilibrium buffer II (urea 6M, SDS 2% (w/v), Tris-HCl(pH 8.8) 0.375M, glycerol 20% (v/v), iodoacetamide 135 mM, bromophenyl blue 3.5M) for 15 minutes. Then, the strip was separated on an SDS-PAGE gel depending on molecular weight.

Proteins were stained by silver staining kit (Amersham Biosciences, Uppsala, Sweden) and 2-D gel was scanned by GS710 Calibrated Imaging Densitometer (Bio-Rad Laboratories Inc., Herculules, Calif.). The number of proteins or spots on gel was measured by software of Melanie II (Bio-Rad Laboratories Inc., Herculules, Calif.) (FIG. 8).

FIG. 8 represents 2-D gel electrophoretic pictures of transformed *E. coli* WIB101 in which IbpA and/or IbpB is overexperssed in vivo. In FIG. 8, (A) represents *E. coli* WIB101(p184ΔCm), (B) represents *E. coli* WIB101(pAC-TacIbpA), (C) represents *E. coli* WIB101(pACTacIbpB), and (D) represents *E. coli* WIB101(pACTacIbpAB). The circles on the 2-D gel represent IbpA and/or IbpB protein.

As shown in FIG. 8, the 2-D gel having many protein spots was obtained from transformed *E. coli* WIB101(pAC-TacIbpA), WIB101(pACTacIbpB) or WIB101 (pACTacIbpAB), compared to the gel obtained from *E. coli* WIB101 (p184ΔCm) as a control.

EXAMPLE 5

The Effect of IbpA, IbpB and HSP26 Upon the 2-D Gel Electrophoresis of *E. coli* W3110

2-D gel electrophoresis for *E. coli* W3110 was performed according to the method described in example 4. First, 2-D gel electrophoresis was carried out to observe the purity of 10 μg purified IbpA or IbpB protein (FIG. 9).

FIG. 9 represents 2-D gel electrophoretic pictures of purified IbpA and IbpB protein. In FIG. 9, (A) and (B) represent IbpA and IbpB, respectively. As shown in FIG. 9, no other proteins except for IbpA and IbpB proteins exist as a result of the 2-D gel electrophoresis. Therefore, it suggests that the purity of IbpA and IbpB is almost 100%.

2-D gel electrophoresis was carried out to observe the effect of sHSPs by adding 10 μg of each of IbpA, IbpB and HSP26 protein to 200 μg of quantified *E. coli* W3110 protein. Moreover, electrophoresis was performed to compare the difference of effects between sHSPs and protease inhibitors, which are generally used to inhibit protein degradation. 200 μg of quantified *E. coli* W3110 protein was used as a control (FIG. 10).

Figure 10:
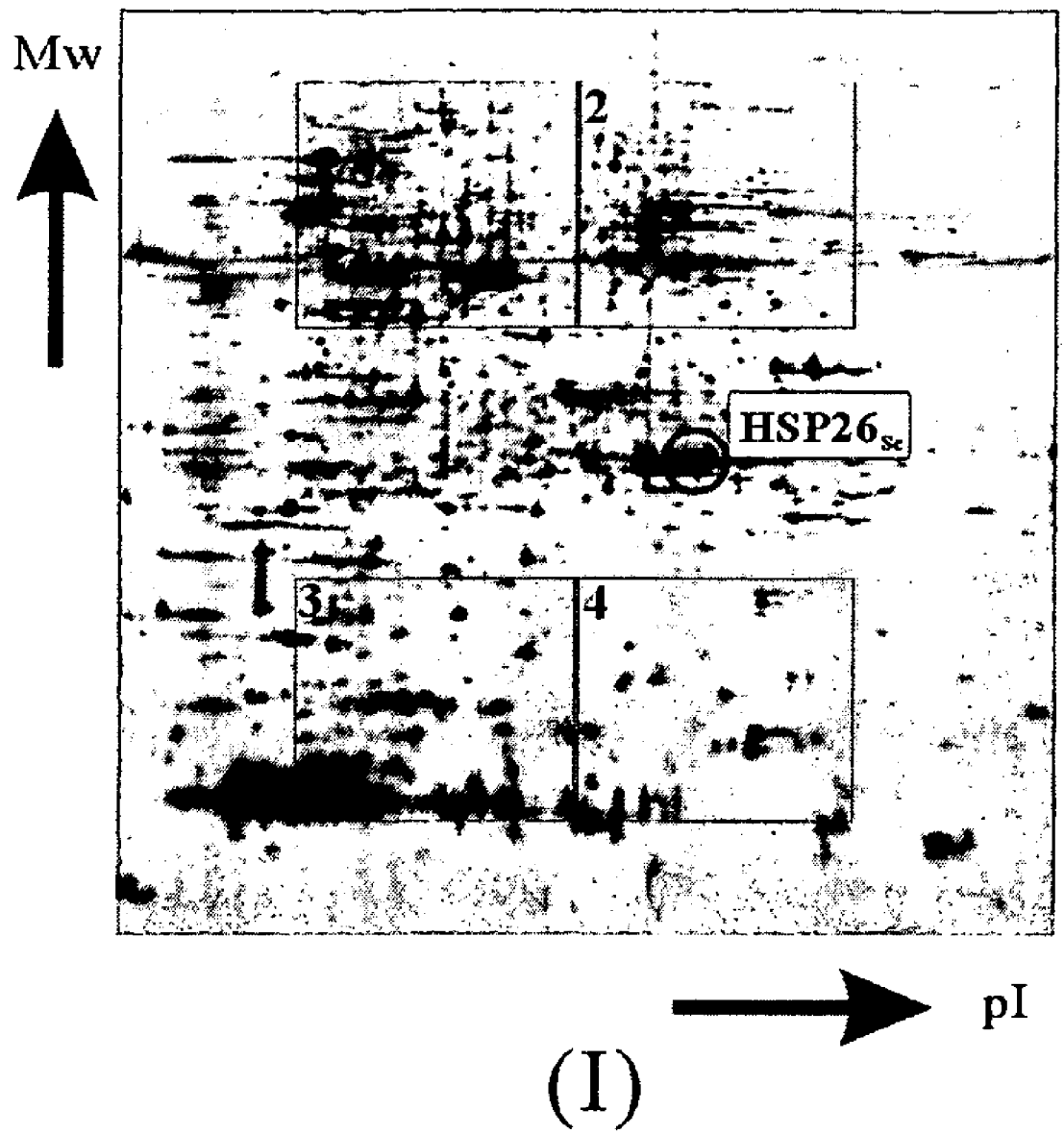
FIG. 10 represents 2-D gel electrophoretic pictures of *E. coli* W3110 adding IbpA, IbpB or HSP26 in vitro. (A) represents *E. coli* W3110 as a control, (B) represents the case of adding 1 mM PMSF to *E. coli* W3110, (C) represents the case of adding 4 mM AEBSF(Pefabloc SC) to *E. coli* W3110, (D) represents the case of adding 1 mM EDTA to *E. coli* W3110, (E) represents the case of adding cocktail inhibitor (7 ml/tablet) to *E. coli* W3110, (F) represents the case of adding 10 μg of IbpA protein to *E. coli* W3110, (G) represents the case of adding 10 μg of IbpB protein to *E. coli* W3110, (H) represents the case of adding 10 μg of IbpA protein derived from *Pseudomonas* to *E. coli* W3110, and (I) represents the case of adding 10 μg of HSP26 protein derived from *Saccharomyces cerevisiae* to *E. coli* W3110.

FIG. 10 represents 2-D gel electrophoretic pictures of *E. coli* W3110 adding IbpA, IbpB or HSP26 in vitro. In FIG. 10, (A) represents *E. coli* W3110 as a control, (B) represents the case of adding 1 mM PMSF to *E. coli* W3110, (C) represents the case of adding 4 mM AEBSF (Pefabloc SC) to *E. coli* W3110, (D) represents the case of adding 1 mM EDTA to *E. coli* W3110, (E) represents the case of adding cocktail inhibitor (7 ml/tablet) to *E. coli* W3110, (F) represents the case of adding 10 μg of IbpA protein to *E. coli* W3110, (G) represents the case of adding 10 μg of IbpB protein to *E. coli* W3110, (H) represents the case of adding 10 μg of IbpA protein derived from *Pseudomonas* to *E. coli* W3110, and (1) represents the case of adding 10 μg of HSP26 protein derived from *Saccharomyces cerevisiae* to *E. coli* W3110.

As shown in FIG. 10, the order of protease inhibitor potency for *E. coli* whole lysate was: sHSPs>Cocktail inhibitor>AEBSF>EDTA>PMSF. PMSF may be unsuitable for 2-D gel electrophoresis application because it rapidly becomes inactive in aqueous solutions and may be less effective in the presence of thiol reagents such as DTT or 2-mercaptoethanol. Cocktail inhibitor or AEBSF can be commonly used in *E. coli* 2-DE even though the choice of protease inhibitor depends on the nature of the protein sample to be solubilized. On the other hand, the 2-D gel electrophoresis added with IbpA, IbpB or HSP26 protein was observed to have many protein spots comparing to the known method.

Figure 11:
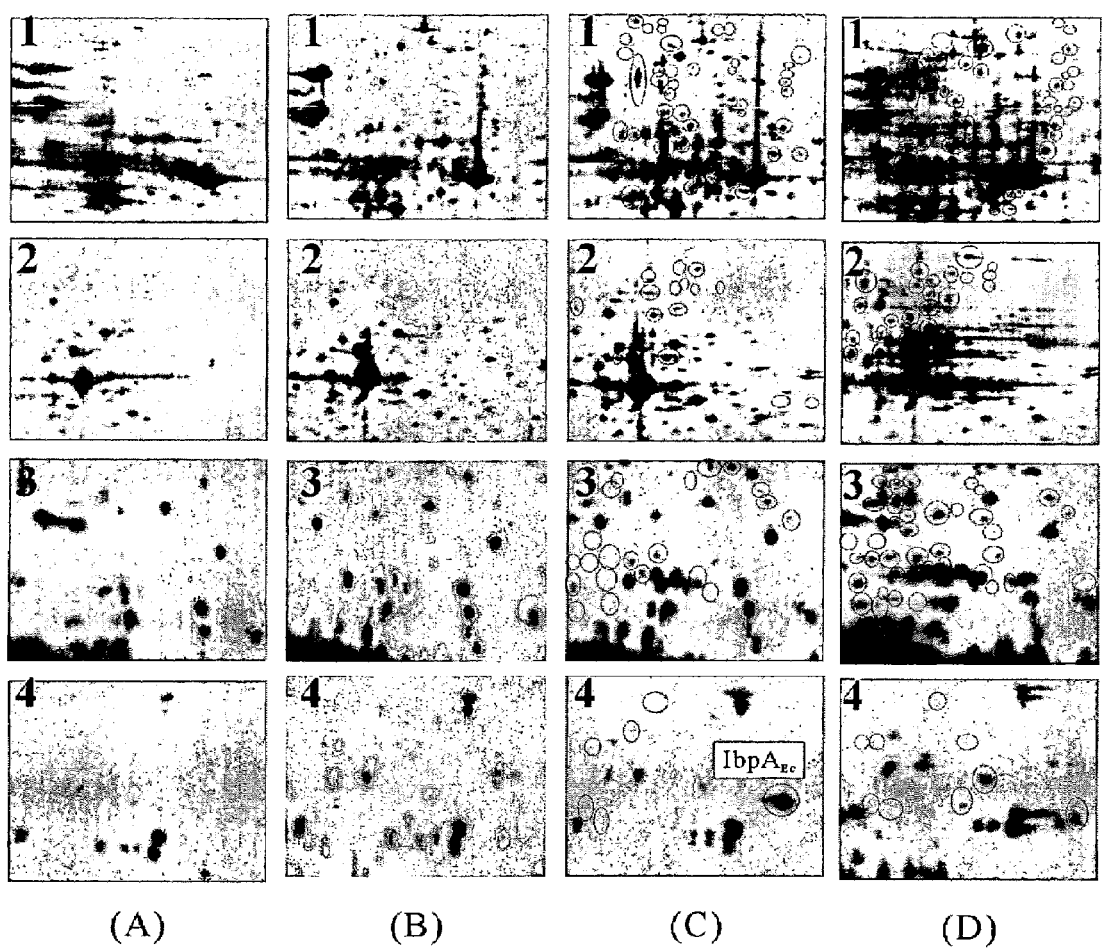
FIG. 11 represents small regions of the gel which were enlarged to allow a better comparison of the separation properties by using sHSPs. (A) represents *E. coli* W3110 as a control, (B) represents the case of adding cocktail inhibitor (7 ml/tablet) to *E. coli* W3110, (C) represents the case of adding 10 μg of IbpA protein to *E. coli* W3110, and (D) represents the case of adding 10 μg of HSP26 protein derived from *Saccharomyces cerevisiae* to *E. coli* W3110.

FIG. 11 represents small regions of the gel which were enlarged to allow a better comparison of the separation properties by using sHSPs. (A) represents *E. coli* W3110 as a control, (B) represents the case of adding cocktail inhibitor (7 ml/tablet) to *E. coli* W3110, (C) represents the case of adding 10 μg of IbpA protein to *E. coli* W3110, and (D) represents the case of adding 10 μg of HSP26 protein derived from *Saccharomyces cerevisiae* to *E. coli* W3110.

As shown in FIG. 11, the number of spots 2-D gels with adding sHSPs was greater than that of 2-D gel without adding sHSPs and spot clearness was far better, which suggests that sHSPs added 2-D gels resolve more protein spots with significant quantitative or qualitative improvement. Therefore, sHSPs prevent losses of both high and small molecular mass proteins.

When compared to commercial protease inhibitors for inhibition of proteolysis during 2-D gel electrophoresis, the sHSPs has several advantages: First, it has better efficiency of inhibition than commercial protease inhibitors. This approach may allow reduction of proteolysis and visualization of a maximal number of protein spots for all kinds of samples. A wide spectrum of vulnerable proteins seems to protect proteolysis because of the broad size distribution of sHSPs complexes. Second, it is much more inexpensive than commercial protease inhibitors. Third, quantification of protein samples can be easily achieved by using known amount of sHSPs added as an internal standard like house keeping enzymes. This is particularly important when we deal with protease-rich samples such as plant extracts, some animal organs including pancreas, stomach, liver, spleen, and samples containing some subcellular organelles as vacuoles and lysosomes. Consequently, sHSPs can be used as new protease inhibitors during preparation of protein complexes.

EXAMPLE 6

The Effect of IbpA Upon the 2-D Gel Electrophoresis of *Pseudomonas*

The 2-D gel electrophoresis for *Pseudomonas putida* KT2440 was performed according to the method described in example 4. The 2-D gel electrophoresis was carried out to observe the effect of IbpA by adding 10 μg of IbpA protein to 200 μg of quantified *Pseudomonas putida* KT2440 protein (FIG. 12). 200 μg of quantified *Pseudomonas putida* KT2440 protein was used as a control.

FIG. 12 represents 2-D gel electrophoretic pictures of *Pseudomonas putida* KT2440. In FIG. 12, (A) represents *Pseudomonas putida* KT2440 as a control, and (B) represents the case of adding 100 μg of IbpA protein to *Pseudomonas putida* KT2440. As shown in FIG. 12, the 2-D gel electrophoresis added with IbpA protein was observed to have much more protein spots.

EXAMPLE 7

The Effect of IbpA and IbpB Upon the 2-D Gel Electrophoresis of Human Serum

The 2-D gel electrophoresis for human serum was performed according to the method described in example 4. The 2-D gel electrophoresis was carried out to observe the effect of IbpA and IbpB by adding 10 μg of IbpA and IbpB protein, respectively, to 200 μg of quantified human serum protein (FIG. 13). 200 μg of quantified human serum protein was used as a control.

FIG. 13 represents 2-D gel electrophoretic pictures of human serum. In FIG. 13, (A) represents human serum as a control, (B) represents the case of adding 10 μg of IbpA protein to human serum, and (C) represents the case of adding 10 μg of IbpB protein to human serum. As shown in FIG. 13, the 2-D gel electrophoresis added with IbpA and IbpB protein was observed to have much more protein spots.

As described above, the present invention has the effect of providing an inventive composition containing sHSPs for prevention of protein degradation and a composition for 2-D gel electrophoresis. Furthermore, decreasing of protein spots was prevented in the 2-D gel electrophoresis using sHSPs such as IbpA, IbpB, IbpAB, HSP26 etc., thereby obtaining 2-D gel with much more protein spots. Therefore, the present invention is expected to provide improvement of studies on proteome in cells.

What is claimed is:

1. A gel electrophoresis sample composition that is resistant to protein degradation, comprising protein that is susceptible to degradation by protease, with protease being present in the sample composition, and with the sample composition containing small heat shock protein (sHSP) added to said protein susceptible to degradation by protease, in an amount in a range of from 0.1 to 50 parts, relative to 100 parts by weight of total protein in said sample composition, wherein said added sHSP includes sHSP selected from the group consisting of:

IbpA (inclusion body-associated protein A) derived from *Agrobacterium tumefaciens;*
sHSPs derived from *Arabidopsis thaliana;*
HspB (heat shock protein B), HspH (heat shock protein H), HspC (heat shock protein C) and
HspF (heat shock protein F) derived from *Bradyrbizobium japonicum;*
IbpA derived from *Brucella suis;*
sHPs derived from *Buchnera aphidicola;*
IbpA derived from *Buchnera aphidicola* str. APS (*Acyrthosiphon pisum*);
sHSPs derived from *Citrus tristeza* virus;
IbpA and IbpB (inclusion body-associated protein B) derived from *Escherichia coli;*
IbpB derived from *Helicobacter pylori;*
Hsp 27 and α,β-crystallin derived from Human;
Hsp 16.5 derived from *Methanococcus jannaschii;*
IbpA derived from *Methanopyrus kandleri;*
Hsp 25 derived from Murine;
sHSPs derived from *Mycobacterium leprae;*
Hsp 16.3 derived from *Mycobacterium tuberculosis;*
IbpB derived from *Pirellula sp.;*
Hspl 8.1 derived from *Pisum sativum*(pea);
sHSPs derived from *Plasmodium falciparum;*
IbpA derived from *Pseudomonas aeruginosa;*
IbpA derived from *Pseudomonas putida;*
Hsp 26 derived from *Saccharomyces cerevisiae;*
IbpA and IbpB derived from *Salmonella enterica;*
IbpA and IbpB derived from *Salmonella typhimurium;*
IbpA derived from *Shewanella oneidensis;*
IbpA and IbpB derived from *Shigella flexneri;*
IbpA derived from *Sinorhizobium meliloti;*
lbpA derived from *Streptococcus pyogenes;*
sHSPs derived from *Streptomyces coelicolor;*
sHSPs derived from *Sulfolobus solfataricus;*
Hspl 6 derived from Synechococcus vulcanus;
IbpA derived from *Thermoanaerobacter tengcongensis;*
IbpA derived from *Thermoplasma acidophilum*; and
sHSPs IbpA and IbpB derived from *Yersinia pestis.*

2. The composition according to claim 1, further comprising an eleetrophoresis gel, and wherein said sHSP added to said protein susceptible to degradation by protease, includes sHSP selected from the group consisting of:
inclusion body-associated protein A, inclusion body-associated protein B, inclusion body-associated protein AB, and heat shock protein 26.

3. A gel electrophoresis sample composition for use in 2-D gel electrophoresis, wherein said composition is resistant to protein degradation, said composition comprising protein that is susceptible to degradation by protease, with protease being present in the sample composition, and with the sample composition containing small heat shock protein (sHSP) added to said protein susceptible to degradation by protease, in an amount in a range of from 0.1 to 50 parts, relative to 100 parts by weight of total protein in said sample composition, wherein said sHSP includes sHSP selected from the group consisting of:

IbpA(inclusion body-associated protein A) derived from *Agrobacterium tumefaciens;*
sHSPs derived from *Arabidopsis thaliana;*
HspB (heat shock protein B), HspH (heat shock protein H), HspC (heat shock protein C) and
HspF (heat shock protein F) derived from *Bradyrbizobium japonicum;*
IbpA derived from *Brucella suis;*
sHPs derived from *Buchnera aphidicola;*
IbpA derived from *Buchnera aphidicola* str. APS (*Acyrthosiphon pisum*);
sHSPs derived from *Citrus tristeza* virus;
IbpA and IbpB (inclusion body-associated protein B) derived from *Escherichia coli;*
IbpB derived from *Helicobacter pylori;*
Hsp 27 and α, β-crystallin derived from Human;
Hspl 6.5 derived from *Methanococcus jannaschii;*
IbpA derived from *Methanopyrus kandleri;*
Hsp 25 derived from Murine;
sHSPs derived from *Mycobacterium leprae;*
Hspl 6.3 derived from *Mycobacterium tuberculosis;*
IbpS derived from *Pirellula sp.;*
Hspl 8.1 derived from *Pisum sativum*(pea);
sHSPs derived from *Plasmodium falciparum;*
IbpA derived from *Pseudomonas aeruginosa;*
IbpA derived from *Pseudomonas putida;*
Hsp 26 derived from *Saccharomyces cerevisiae;*
IbpA and IbpS derived from *Salmonella enterica;*
IbpA and IbpS derived from *Salmonella typhimurium;*
IbpA derived from *Shewanella oneidensis;*
IbpA and IbpS derived from *Shigella flexneri;*
IbpA derived from *Sinorhizobium meliloti;*
IbpA derived from *Streptococcus pyogenes;*
sHSPs derived from *Streptomyces coelicolor;*
sHSPs derived from *Sulfolobus solfataricus;*
Hspl 6 derived from *Synechococcus vulcanus;*
IbpA derived from *Thermoanaerobacter tengcongensis;*
IbpA derived from *Thermoplasma acidophilum;* and
sHSPs IbpA and IbpB derived from *Yersinia pestis.*

4. The composition according to claim 3, wherein said sHSP added to said protein susceptible to degradation by protease, includes sHSP selected from the group consisting of IbpA, IbpB, IbpAB and HSP 26.

5. A method for the 2-D gel electrophoresis of a gel electrophoresis sample composition comprising protein that is susceptible to degradation by protease, with protease being present in the sample composition, said method comprising:

adding small heat shock protein (sHSP) to the sample composition in an amount in a range of from 0.1 to 50 parts, relative to 100 parts by weight of total protein in said sample composition, so as to prevent protein degradation and obtain a gel with an increased number of spots as compared to a gel obtained for a corresponding sample composition lacking said added small heat shock protein, wherein said added sHSP includes sHSP selected from the group consisting of:

IbpA(inclusion body-associated protein A) derived from *Agrobacterium tumefaciens;*
sHSPs derived from *Arabidopsis thaliana;*
HspB (heat shock protein B), HspH (heat shock protein H), HspC (heat shock protein C) and
HspF (heat shock protein F) derived from *Bradyrbizobium japonicum;*
IbpA derived from *Brucella suis;*
sHPs derived from *Buchnera aphidicola;*
IbpA derived from *Buchnera aphidicola* str. APS (*Acyrthosaphon pisum*);
sHSPs derived from *Citrus tristeza* virus;
IbpA and IbpB (inclusion body-associated protein B) derived from *Escherichia coli;*
IbpB derived from *Helicobacter pylori;*
Hsp 27 and α, β-crystallin derived from Human;
Hspl 6.5 derived from *Methanococcus jannaschii;*
IbpA derived from *Methanopyrus kandleri;*
Hsp 25 derived from Murine;
sHSPs derived from *Mycobacterium leprae;*
Hspl 6.3 derived from *Mycobacterium tuberculosis;*
IbpB derived from *Pirellula sp.;*
Hspl 8.1 derived from *Pisum sativum*(pea);
sHSPs derived from *Plasmodium falciparum;*
IhpA derived from *Pseudomonas aeruginosa;*
IbpA derived from *Pseudomonas putida;*
Hsp 26 derived from *Saccharomyces cerevisiae;*
IbpA and IbpB derived from *Salmonella enterica;*
IbpA and IbpB derived from *Salmonella typhimurium;*
IbpA derived from *Shewanella oneidensis;*
IbpA and IbpB derived from *Shigella flexneri;*
IbpA derived from *Sinorhizobium meliloti;*
IbpA derived from *Streptococcus pyogenes;*
sHSPs derived from *Streptomyces coelicolor;*
sHSPs derived from *Sulfolobus solfataricus;*
Hspl 6 derived from *Synechococcus vulcanus;*
IbpA derived from *Thermoanaerobacter tengcongensis;*
IbpA derived from *Thermoplasma acidophilum;* and
sHSPs IbpA and IbpB derived from *Yersinia pestis;* and
subjecting the composition comprising said at least one small heat shock protein to 2-D gel electrophoresis.

6. A method for the 2-D gel electrophoresis of a gel electrophoresis sample composition comprising protein that is susceptible to degradation by protease, with protease being present in the sample composition, which comprises:

adding small heat shock protein (sHSP) to the sample composition, so as to prevent protein degradation and obtain a gel with an increased number of spots as compared to a gel of a corresponding sample composition lacking added sHSP; and subjecting the sample composition comprising the added sHSP to 2-D gel electrophoresis, wherein the added sHSP comprises sHSP selected from the group consisting of inclusion body-associated protein A (IbpA), inclusion body-associated protein B (IbpB) and inclusion body-associated protein AB (IbpAB) derived from *E. coil,* inclusion body-associated protein A (IbpA) derived from *Pseudomonas* and heat shock protein 26 (HSP26) derived from *Saccharomyces cerevisiae.*

7. The method according to claim 5, wherein the amount of the sHSP that is added is in a range of 0.1 to 50 parts, relative to 100 parts by weight of the total protein of an electrophoresis sample.

8. The method according to claim 7, wherein the amount of the sHSP that is added is 0.5 to 20 parts, relative to 100 parts by weight of the total protein.

9. The method according to claim 5, wherein said composition comprises cells of prokaryotes or eukaryotes.

10. The method according to claim 9, wherein the prokaryotes are *E. coli* or *Pseudomonas* sp. microorganisms, and the eukaryotes are human-derived cells.

11. A method for the analysis of proteomes by 2-D gel electrophoresis, which is characterized by using the composition of claim 1.

12. A method for the 2-D gel electrophoresis of a sample composition comprising protein that is susceptible to degradation by protease, with protease being present in the sample composition, which comprises:
   adding small heat shock protein (sHSP) to the sample composition, so as to prevent protein degradation and obtain a gel with an increased number of spots as compared to a gel of a corresponding sample composition lacking added sHSP; and
   subjecting the mixture comprising the added sHSP to 2-D gel electrophoresis, wherein the added sHSP comprises small heat shock protein (sHSP) derived from an organism selected from the group consisting of *Agrobacterium tumefaciens* str. C58 (U. Washington), *Arabidopsis thaliana Bradyrbizobium japonicum, Brucella suis* 1330, *Buchnera aphidicola* plasmid pBPS1, *Buchnera aphidicola* str. APS (*Acyrthosiphon pisum*), *Citrus tristeza* virus, *Escherichia coli* CFT073, *Escherichia coli* K12, *Escherichia coli* O157:H7 EDL933, *Escherichia coli* O157:H7, *Helicobacter pylori* 26695, Human, *Methanococcus jannaschii*, Murine, *Mycobacterium leprae* strain TN, *Mycobacterium tuberculosis, Pirellula* sp., *Pisum sativum*(pea), *Plasmodium falciparum* 3D7, *Pseudomonas aeruginosa* PA01, *Pseudomonas putida* KT2440, *Saccharomyces cerevisiae, Salmonella enterica* subsp. *enterica* serovar *Typhi Salmonella typhimurium* LT2, *Shewanella oneidensis* MR-1, *Shigella flexneri* 2a str. 2457T, *Shigella flexneri* 2a str. 301, *Sinorhizobium meliloti* 1021, *Sinorhizobium meliloti* plasmid pSymA, *Streptococcus pyogenes, Streptomyces coelicolor* A3(2), *Sulfolobus solfataricus, Synechococcus vulcanus, Thermoanaerobacter tengcongensis* strain MB4T, *Thermoplasma acidophilum, Yersinia pestis* KIM, and *Yersinia pestis* strain CO92.

* * * * *

UNITED STATES PATENT AND TRADEMARK OFFICE
CERTIFICATE OF CORRECTION

PATENT NO. : 7,148,334 B2  
APPLICATION NO. : 10/791059  
DATED : December 12, 2006  
INVENTOR(S) : Sang Yup Lee et al.

It is certified that error appears in the above-identified patent and that said Letters Patent is hereby corrected as shown below:

On Title Page item 56

At page 1, second column, in the FOREIGN PATENT DOCUMENTS,
"WO-02-090966 A1" should be -- WO-02/090966 A1 --

Column 11, line 6, a paragraph break should be inserted before "As shown in FIG. 6,".
Column 13, line 65, "(1)" should be -- (I) --.
Column 14, line 64, "100 µg" should be -- 10 µg --.
Column 18, line 40 (claim 1), "Hspl 8.1" should be -- Hsp 18.1 --.
Column 18, line 54 (claim 1), "Hspl 6" should be -- Hsp 16 --.
Column 18, line 59 (claim 2), "eleetrophoresis" should be -- electrophoresis --.
Column 19, line 26 (claim 3), "Hspl 6.5" should be -- Hsp 16.5 --.
Column 19, line 30 (claim 3), "Hspl 6.3" should be -- Hsp 16.3 --.
Column 19, line 32 (claim 3), "Hspl 8.1" should be -- Hsp 18.1 --.
Column 19, line 37 (claim 3), "IbpS" should be -- IbpB --.
Column 19, line 38 (claim 3), "IbpS" should be -- IbpB --.
Column 19, line 40 (claim 3), "IbpS" should be -- IbpB --.
Column 19, line 45 (claim 3), "Hspl 6" should be -- Hsp 16 --.
Column 20, line 11 (claim 3), "Acyrthosaphon" should be -- Acyrthosiphon --.
Column 20, line 17 (claim 5), "Hspl 6.5" should be -- Hsp 16.5 --.
Column 20, line 21 (claim 5), "Hspl 6.3" should be -- Hsp 16.3 --.
Column 20, line 23 (claim 5), "Hspl 8.1" should be -- Hsp 18.1 --.
Column 20, line 25 (claim 5), "IhpA" should be -- IbpA --.
Column 20, line 36 (claim 5), "Hspl 6" should be -- Hsp 16 --.
Column 20, line 57 (claim 5), "E. coil" should be -- E. coli --.

Signed and Sealed this

Thirteenth Day of March, 2007

JON W. DUDAS  
*Director of the United States Patent and Trademark Office*